(12) United States Patent
Newton et al.

(10) Patent No.: US 9,314,294 B2
(45) Date of Patent: Apr. 19, 2016

(54) ENHANCED CONTROL SYSTEMS INCLUDING FLEXIBLE SHIELDING AND SUPPORT SYSTEMS FOR ELECTROSURGICAL APPLICATIONS

(71) Applicant: Encision, Inc., Boulder, CO (US)

(72) Inventors: David Newton, Longmont, CO (US); Warren Taylor, Longmont, CO (US)

(73) Assignee: ENCISION, INC., Boulder, CO (US)

( * ) Notice: Subject to any disclaimer, the term of this patent is extended or adjusted under 35 U.S.C. 154(b) by 325 days.

(21) Appl. No.: 13/788,714

(22) Filed: Mar. 7, 2013

(65) Prior Publication Data
US 2013/0317496 A1    Nov. 28, 2013

Related U.S. Application Data

(62) Division of application No. 12/543,344, filed on Aug. 18, 2009, now Pat. No. 8,500,728.

(60) Provisional application No. 61/089,668, filed on Aug. 18, 2008.

(51) Int. Cl.
A61B 18/12    (2006.01)
A61B 18/14    (2006.01)
(Continued)

(52) U.S. Cl.
CPC .............. *A61B 18/14* (2013.01); *A61B 18/1445* (2013.01); *A61B 19/2203* (2013.01); *A61B 17/3421* (2013.01); *A61B 18/1233* (2013.01); *A61B 18/16* (2013.01); *A61B 2017/00026* (2013.01); *A61B 2017/00039* (2013.01); *A61B 2017/00323* (2013.01); *A61B 2017/2927* (2013.01); *A61B 2017/3445* (2013.01);
(Continued)

(58) Field of Classification Search
CPC .............. A61B 18/1233; A61B 18/16; A61B 2018/00892; A61B 2018/00666; A61B 2018/167
USPC .................... 606/34, 35, 38, 41, 42
See application file for complete search history.

(56) References Cited

U.S. PATENT DOCUMENTS

| 984,756 A | 2/1911 | Frisch |
| 1,754,806 A | 4/1930 | Stevenson |

(Continued)

FOREIGN PATENT DOCUMENTS

| DE | 1139927 | 8/1961 |
| DE | 3013784 | 10/1980 |

(Continued)

OTHER PUBLICATIONS

Peffley, Michael F. , "Office Action re U.S. Appl. No. 11/202,915", Jan. 8, 2008, p. 3, Published in: US.

(Continued)

*Primary Examiner* — Michael Peffley
*Assistant Examiner* — Thomas Giuliani
(74) *Attorney, Agent, or Firm* — Neugeboren O'Dowd PC

(57) ABSTRACT

A surgical system comprises a device adapted to deliver a plurality of surgical instruments to a site within a patient's body, a first surgical instrument comprising an active electrode probe, a second surgical instrument for performing a non-electrosurgical procedure, a conductive shield surrounding the active electrode probe of the first surgical instrument and connected to a reference potential, and a cold instrument monitor connected to the second surgical instrument and to the reference potential.

21 Claims, 15 Drawing Sheets

(51) Int. Cl.
  *A61B 19/00* (2006.01)
  *A61B 17/34* (2006.01)
  *A61B 18/16* (2006.01)
  *A61B 17/00* (2006.01)
  *A61B 17/29* (2006.01)
  *A61B 18/00* (2006.01)

(52) U.S. Cl.
  CPC . *A61B2017/3449* (2013.01); *A61B 2017/3466* (2013.01); *A61B 2018/00827* (2013.01); *A61B 2018/00875* (2013.01); *A61B 2018/00892* (2013.01); *A61B 2018/167* (2013.01); *A61B 2019/2234* (2013.01); *A61B 2019/2238* (2013.01); *A61B 2019/2242* (2013.01); *A61B 2019/4081* (2013.01); *A61B 2019/448* (2013.01)

(56) References Cited

U.S. PATENT DOCUMENTS

| | | |
|---|---|---|
| 2,004,559 A | 6/1935 | Wappler et al. |
| 2,008,367 A | 7/1935 | Rhinevault |
| 2,448,741 A | 9/1948 | Scott et al. |
| 2,741,248 A | 4/1956 | Woodhall |
| 3,070,132 A | 12/1962 | Sheridan |
| 3,580,983 A | 5/1971 | Jackson |
| 3,585,985 A | 6/1971 | Gould |
| 3,601,126 A | 8/1971 | Estes |
| 3,706,008 A | 12/1972 | Kremer |
| 3,707,149 A | 12/1972 | Hao et al. |
| 3,804,096 A | 4/1974 | Gonser |
| 3,834,392 A | 9/1974 | Lampman et al. |
| 3,838,242 A | 9/1974 | Goucher |
| 3,895,635 A | 7/1975 | Justus et al. |
| 3,898,991 A | 8/1975 | Ikuno et al. |
| 3,905,373 A | 9/1975 | Gonser |
| 3,913,583 A | 10/1975 | Bross |
| 3,933,157 A | 1/1976 | Bjurwill et al. |
| 3,946,738 A | 3/1976 | Newton et al. |
| 3,963,856 A | 6/1976 | Carlson et al. |
| 3,974,833 A | 8/1976 | Durden, III |
| 3,994,287 A | 11/1976 | Turp et al. |
| 4,003,380 A | 1/1977 | Wien |
| 4,043,342 A | 8/1977 | Morrison, Jr. |
| 4,084,594 A | 4/1978 | Mosior |
| 4,181,131 A | 1/1980 | Ogiu |
| 4,184,492 A | 1/1980 | Meinke et al. |
| 4,200,104 A | 4/1980 | Harris |
| 4,231,372 A | 11/1980 | Newton |
| 4,232,676 A | 11/1980 | Herczog |
| 4,237,887 A | 12/1980 | Gonser |
| 4,248,716 A | 2/1981 | LaValley |
| 4,303,073 A | 12/1981 | Archibald |
| 4,311,144 A | 1/1982 | Harada |
| 4,325,374 A | 4/1982 | Komiya |
| 4,343,308 A | 8/1982 | Gross |
| 4,367,746 A | 1/1983 | Derechinsky |
| 4,374,517 A | 2/1983 | Hagiwara |
| 4,427,006 A | 1/1984 | Nottke |
| 4,433,687 A | 2/1984 | Burke et al. |
| 4,440,170 A | 4/1984 | Golden et al. |
| 4,449,532 A | 5/1984 | Storz |
| 4,494,541 A | 1/1985 | Archibald |
| 4,562,838 A | 1/1986 | Walker |
| 4,581,021 A | 4/1986 | Landau et al. |
| 4,601,710 A | 7/1986 | Moll |
| 4,615,330 A | 10/1986 | Nagasaki et al. |
| 4,617,927 A | 10/1986 | Manes |
| 4,618,885 A | 10/1986 | Nagasaki et al. |
| 4,638,802 A | 1/1987 | Okada |
| 4,657,015 A | 4/1987 | Irnich |
| 4,662,369 A | 5/1987 | Ensslin |
| 4,674,501 A | 6/1987 | Greenberg |
| 4,716,897 A | 1/1988 | Noguchi et al. |
| 4,719,914 A | 1/1988 | Johnson |
| 4,741,334 A | 5/1988 | Irnich |
| 4,744,361 A | 5/1988 | Karasawa |
| 4,781,175 A | 11/1988 | Bertrand et al. |
| 4,787,891 A | 11/1988 | Harding et al. |
| 4,800,869 A | 1/1989 | Nakajima |
| 4,818,954 A | 4/1989 | Flachenecker et al. |
| 4,832,048 A | 5/1989 | Cohen |
| 4,844,063 A | 7/1989 | Clark |
| 4,886,505 A | 12/1989 | Haynes et al. |
| 4,919,129 A | 4/1990 | Weber, Jr. et al. |
| 4,932,952 A | 6/1990 | Wojciechowicz, Jr. |
| 4,983,456 A | 1/1991 | Iwaskow et al. |
| 4,998,933 A | 3/1991 | Eggers et al. |
| 5,007,257 A | 4/1991 | Thompson |
| 5,009,643 A | 4/1991 | Reich et al. |
| 5,009,656 A | 4/1991 | Reimels |
| 5,084,045 A | 1/1992 | Helenowski |
| 5,087,257 A | 2/1992 | Farin et al. |
| 5,089,002 A | 2/1992 | Kirwan, Jr. |
| RE33,925 E | 5/1992 | Bales et al. |
| 5,116,353 A | 5/1992 | Green |
| 5,147,357 A | 9/1992 | Rose et al. |
| 5,152,762 A | 10/1992 | McElhenney |
| 5,176,702 A | 1/1993 | Bales et al. |
| 5,178,620 A | 1/1993 | Eggers et al. |
| 5,263,967 A | 11/1993 | Lyons, III et al. |
| 5,275,615 A | 1/1994 | Rose |
| 5,277,696 A | 1/1994 | Hagen |
| 5,281,216 A | 1/1994 | Klicek |
| 5,295,993 A | 3/1994 | Green |
| 5,308,358 A | 5/1994 | Bond et al. |
| 5,312,401 A * | 5/1994 | Newton et al. ............... 606/46 |
| 5,318,516 A | 6/1994 | Cosmescu |
| 5,334,198 A | 8/1994 | Hart et al. |
| 5,342,357 A | 8/1994 | Nardella |
| 5,344,428 A | 9/1994 | Griffiths |
| 5,366,443 A | 11/1994 | Eggers et al. |
| 5,383,876 A | 1/1995 | Nardella |
| 5,396,900 A | 3/1995 | Kratsch et al. |
| 5,403,311 A | 4/1995 | Abele et al. |
| 5,419,767 A | 5/1995 | Eggers et al. |
| 5,423,811 A | 6/1995 | Imran et al. |
| 5,431,638 A | 7/1995 | Hennig et al. |
| 5,432,549 A | 7/1995 | Hassler et al. |
| 5,436,566 A | 7/1995 | Thompson et al. |
| 5,443,463 A | 8/1995 | Marion et al. |
| 5,449,356 A | 9/1995 | Bowers et al. |
| 5,496,317 A | 3/1996 | Goble et al. |
| 5,520,685 A | 5/1996 | Wojciechowicz |
| 5,531,676 A | 7/1996 | Edwards et al. |
| 5,558,671 A | 9/1996 | Yates |
| 5,571,137 A | 11/1996 | Marlow et al. |
| 5,599,350 A | 2/1997 | Schulze et al. |
| 5,609,601 A | 3/1997 | Aranyi et al. |
| 5,626,608 A | 5/1997 | Aranyi et al. |
| 5,674,220 A | 10/1997 | Fox et al. |
| 5,683,366 A | 11/1997 | Eggers et al. |
| 5,688,269 A | 11/1997 | Newton et al. |
| 5,688,270 A | 11/1997 | Yates et al. |
| 5,693,051 A | 12/1997 | Schulze et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,709,680 A | 1/1998 | Yates et al. |
| 5,720,744 A | 2/1998 | Eggleston et al. |
| 5,731,896 A | 3/1998 | Baumann et al. |
| 5,735,849 A | 4/1998 | Baden et al. |
| 5,752,951 A | 5/1998 | Yanik |
| 5,766,165 A | 6/1998 | Gentelia et al. |
| 5,766,167 A | 6/1998 | Eggers et al. |
| 5,769,841 A | 6/1998 | Odell et al. |
| 5,772,659 A | 6/1998 | Becker et al. |
| 5,776,130 A | 7/1998 | Buysse et al. |
| 5,792,141 A | 8/1998 | Logeman |
| 5,797,941 A | 8/1998 | Fox et al. |
| 5,800,449 A | 9/1998 | Wales |
| 5,817,093 A | 10/1998 | Williamson, IV et al. |

(56) References Cited

U.S. PATENT DOCUMENTS

| | | | |
|---|---|---|---|
| 5,827,271 A | 10/1998 | Buysse et al. | |
| 5,833,690 A | 11/1998 | Yates et al. | |
| 5,868,742 A * | 2/1999 | Manes et al. | 606/46 |
| 5,919,191 A | 7/1999 | Lennox et al. | |
| 5,954,686 A | 9/1999 | Ellman et al. | |
| 5,976,128 A | 11/1999 | Schilling et al. | |
| 6,001,096 A | 12/1999 | Bissinger et al. | |
| 6,024,741 A | 2/2000 | Williamson, IV et al. | |
| 6,039,732 A | 3/2000 | Ichikawa et al. | |
| 6,059,781 A | 5/2000 | Patil et al. | |
| 6,063,075 A | 5/2000 | Mihori | |
| 6,086,586 A | 7/2000 | Hooven | |
| 6,113,597 A | 9/2000 | Eggers et al. | |
| 6,142,992 A * | 11/2000 | Cheng | A61B 18/1206 606/34 |
| 6,174,309 B1 | 1/2001 | Wrublewski et al. | |
| 6,228,080 B1 | 5/2001 | Gines | |
| 6,228,083 B1 | 5/2001 | Lands et al. | |
| 6,238,388 B1 | 5/2001 | Ellman et al. | |
| 6,245,063 B1 | 6/2001 | Uphoff | |
| 6,273,887 B1 | 8/2001 | Yamauchi et al. | |
| 6,277,114 B1 | 8/2001 | Bullivant et al. | |
| 6,398,779 B1 | 6/2002 | Buysse et al. | |
| 6,409,728 B1 | 6/2002 | Ehr et al. | |
| 6,436,096 B1 | 8/2002 | Hareyama | |
| 6,440,130 B1 | 8/2002 | Mulier et al. | |
| 6,451,018 B1 | 9/2002 | Lands et al. | |
| 6,458,130 B1 | 10/2002 | Frazier et al. | |
| 6,471,701 B2 | 10/2002 | Brommersma et al. | |
| 6,500,176 B1 | 12/2002 | Truckai et al. | |
| 6,502,608 B1 | 1/2003 | Burchett et al. | |
| 6,511,476 B2 | 1/2003 | Hareyama | |
| 6,582,451 B1 | 6/2003 | Marucci et al. | |
| 6,585,735 B1 | 7/2003 | Frazier et al. | |
| 6,620,157 B1 | 9/2003 | Dabney et al. | |
| 6,634,924 B1 | 10/2003 | Ono et al. | |
| 6,682,527 B2 | 1/2004 | Strul | |
| 6,682,528 B2 | 1/2004 | Frazier et al. | |
| 6,695,840 B2 | 2/2004 | Schulze | |
| 6,730,080 B2 | 5/2004 | Harano et al. | |
| 6,733,498 B2 | 5/2004 | Paton et al. | |
| 6,743,230 B2 | 6/2004 | Lutze et al. | |
| 6,767,349 B2 | 7/2004 | Ouchi | |
| 6,796,981 B2 | 9/2004 | Wham et al. | |
| 6,802,843 B2 | 10/2004 | Truckai et al. | |
| 6,817,974 B2 | 11/2004 | Cooper et al. | |
| 6,827,717 B2 | 12/2004 | Brommersma et al. | |
| 6,830,569 B2 | 12/2004 | Thompson et al. | |
| 6,855,142 B2 | 2/2005 | Harano et al. | |
| 6,890,331 B2 | 5/2005 | Kristensen | |
| 6,905,497 B2 | 6/2005 | Truckai et al. | |
| 6,929,641 B2 | 8/2005 | Goble et al. | |
| 6,929,643 B2 | 8/2005 | Ohyama et al. | |
| 6,929,644 B2 | 8/2005 | Truckai et al. | |
| 6,984,231 B2 | 1/2006 | Goble et al. | |
| 7,011,657 B2 | 3/2006 | Truckai et al. | |
| 7,052,496 B2 | 5/2006 | Yamauchi | |
| 7,083,618 B2 | 8/2006 | Couture et al. | |
| 7,083,619 B2 | 8/2006 | Truckai et al. | |
| 7,089,054 B2 | 8/2006 | Palti | |
| 7,090,673 B2 | 8/2006 | Couture et al. | |
| 7,094,231 B1 | 8/2006 | Ellman et al. | |
| 7,101,371 B2 | 9/2006 | Dycus et al. | |
| 7,101,372 B2 | 9/2006 | Brown et al. | |
| 7,101,373 B2 | 9/2006 | Brown et al. | |
| 7,112,199 B2 | 9/2006 | Cosmescu | |
| 7,112,201 B2 | 9/2006 | Truckai et al. | |
| 7,115,121 B2 | 10/2006 | Novak | |
| 7,118,587 B2 | 10/2006 | Dycus | |
| 7,131,445 B2 | 11/2006 | Amoah | |
| 7,131,971 B2 | 11/2006 | Couture et al. | |
| 7,135,020 B2 | 11/2006 | Buysse et al. | |
| 7,147,638 B2 | 12/2006 | Chapman et al. | |
| 7,150,097 B2 | 12/2006 | Hampton et al. | |
| 7,150,749 B2 | 12/2006 | Dycus et al. | |
| 7,153,300 B2 | 12/2006 | Goble | |
| 7,156,846 B2 | 1/2007 | Dycus et al. | |
| 7,160,298 B2 | 1/2007 | Lawes et al. | |
| 7,160,299 B2 | 1/2007 | Baily | |
| 7,169,146 B2 | 1/2007 | Truckai et al. | |
| 7,179,258 B2 | 2/2007 | Buysse et al. | |
| 7,186,253 B2 | 3/2007 | Truckai et al. | |
| 7,186,261 B2 | 3/2007 | Prestel | |
| 7,189,233 B2 | 3/2007 | Truckai et al. | |
| 7,195,631 B2 | 3/2007 | Dumbauld | |
| 7,203,556 B2 | 4/2007 | Daners | |
| 7,204,835 B2 | 4/2007 | Latterell et al. | |
| 7,207,990 B2 | 4/2007 | Cunningham et al. | |
| 7,211,081 B2 | 5/2007 | Goble | |
| 7,211,084 B2 | 5/2007 | Goble et al. | |
| 7,214,224 B2 | 5/2007 | Goble | |
| 7,422,589 B2 | 9/2008 | Newton et al. | |
| 7,465,302 B2 | 12/2008 | Newton et al. | |
| 2001/0056279 A1 | 12/2001 | Odell et al. | |
| 2002/0165541 A1 | 11/2002 | Whitman | |
| 2003/0073987 A1 | 4/2003 | Sakurai et al. | |
| 2004/0019348 A1 | 1/2004 | Gifford et al. | |
| 2004/0019351 A1 | 1/2004 | Harano et al. | |
| 2004/0167515 A1 | 8/2004 | Manzo et al. | |
| 2004/0193148 A1 | 9/2004 | Buysse et al. | |
| 2004/0267256 A1 | 12/2004 | Garabedian et al. | |
| 2005/0013190 A1 | 1/2005 | Beatty et al. | |
| 2005/0021027 A1 | 1/2005 | Meagher et al. | |
| 2005/0113827 A1 | 5/2005 | Dumbauld et al. | |
| 2005/0137590 A1 | 6/2005 | Cosgriff et al. | |
| 2005/0187547 A1 | 8/2005 | Sugi | |
| 2005/0203504 A1 | 9/2005 | Wham et al. | |
| 2005/0251134 A1 | 11/2005 | Davison et al. | |
| 2005/0256522 A1 | 11/2005 | Francischelli et al. | |
| 2006/0041252 A1 | 2/2006 | Newton et al. | |
| 2006/0041253 A1 | 2/2006 | Odell et al. | |
| 2006/0079876 A1 | 4/2006 | Barton et al. | |
| 2006/0111210 A1 | 5/2006 | Hinman | |
| 2006/0129146 A1 | 6/2006 | Dycus et al. | |
| 2006/0161136 A1 | 7/2006 | Anderson et al. | |
| 2006/0167450 A1 | 7/2006 | Buysse et al. | |
| 2006/0173452 A1 | 8/2006 | Buysse et al. | |
| 2006/0224158 A1 | 10/2006 | Hammill et al. | |
| 2006/0293656 A1 | 12/2006 | Shadduck et al. | |
| 2007/0043353 A1 | 2/2007 | Dycus et al. | |
| 2007/0066969 A1 | 3/2007 | McGreevy et al. | |
| 2007/0078456 A1 | 4/2007 | Dumbauld et al. | |
| 2007/0106297 A1 | 5/2007 | Dumbauld et al. | |
| 2009/0192524 A1 | 7/2009 | Dimaio et al. | |

FOREIGN PATENT DOCUMENTS

| | | |
|---|---|---|
| DE | 4419070 | 12/1994 |
| JP | 53-13583 A | 2/1978 |
| JP | 52-47278 A | 12/1998 |
| WO | 2010022088 A1 | 2/2010 |

OTHER PUBLICATIONS

Peffley, Michael F. , "Office Action re U.S. Appl. No. 11/202,915", Apr. 23, 2007, p. 6, Published in: US.

Giuliani, Thomas Anthony, "Office Action re U.S. Appl. No. 12/543,344", May 10, 2012, p. 10, Published in: US.

Giuliani, Thomas Anthony, "Office Action re U.S. Appl. No. 12/543,344", Jul. 30, 2012, p. 29, Published in: US.

Papapietro, Jacqueline M., "Office Action re U.S. Appl. No. 11/202,458", Aug. 17, 2007, p. 13, Published in: US.

Dicicco, John R., "Office Action re U.S. Appl. No. 11/202,605", Oct. 25, 2007, p. 7, Published in: US.

Peffley, Michael F., "Office Action re U.S. Appl. No. 11/202,915", Nov. 1, 2007, p. 1, Published in: US.

O'Dowd, Sean R., "Response to Office Action re U.S. Appl. No. 11/202,458", Jan. 17, 2008, p. 15, Published in: US.

O'Dowd, Sean R., "Response to Office Action re U.S. Appl. No. 11/202,605", Feb. 24, 2008, p. 8, Published in: US.

O'Dowd, Sean R., "Response to Office Action re U.S. Appl. No. 11/202,915", Mar. 3, 2008, p. 9, Published in: US.

(56) References Cited

OTHER PUBLICATIONS

O'Dowd, Sean R., "Response to Office Action re U.S. Appl. No. 11/202,915", Sep. 24, 2007, p. 13, Published in: US.

O'Dowd, Sean R., "Response to Office Action re U.S. Appl. No. 11/202,915", Dec. 31, 2007, p. 3, Published in: US.

Young, Lee W., "PCT/US/09154206 International Search Report, dated Dec. 3, 2009", p. 10, Published in: US.

Beijer, Gijsbertus, "International Preliminary Report on Patentability re Application No. PCT/US09/54206", Feb. 22, 2011, p. 9, Published in: CH.

Viegas Da Cruz, Isabel, "Notification of Transmittal of the International Search Report and Written Opinion re Application No. PCT/US05/029016", Apr. 12, 2006, p. 16, Published in: PCT.

Nickitas-Etienne, Athina, "International Preliminary Report of Patentability re Application No. PCT/US2005/029016", Mar. 1, 2007, p. 10, Published in: CH.

Neugeboren, Craig, "Response to Office Action re U.S. Appl. No. 12/543,344", May 30, 2012, p. 10, Published in: US.

Neugeboren, Craig, "Response to Office Action re U.S. Appl. No. 12/543,344", Dec. 30, 2012, p. 13, Published in: US.

\* cited by examiner

ENHANCED CONTROL SYSTEMS INCLUDING FLEXIBLE SHIELDING AND SUPPORT SYSTEMS FOR ELECTROSURGICAL APPLICATIONS

PRIORITY AND RELATED APPLICATIONS

This application is a divisional application of, and claims the benefit of, U.S. application Ser. No. 12/543,344 filed on Aug. 18, 2009 now U.S. Pat. No. 8,500,728, issued Aug. 6, 2013, and also claims the benefit of Provisional U.S. Application No. 61/089,668 filed on Aug. 18, 2008. The details of Application No. 61/089,668 and Ser. No. 12/543,344 are incorporated by reference into the present application in their entirety and for all proper purposes.

FIELD OF THE INVENTION

Aspects of the present invention relate to electrosurgical procedures, techniques, and devices that utilize enhanced control systems such as robotics and other motion control apparatus. Aspect of the present invention also relate to electrosurgical systems with a monitored safety system capable of monitoring both the electrosurgical instruments and any neutral instruments or other conductive surfaces in the general vicinity of the surgical site.

BACKGROUND

Enhanced control surgery (ECS) systems broadly refers to devices and systems that consist of mechanical or electro-mechanical configurations and that may provide one or more enhanced endo-mechanical features that enable a surgeon with improved surgical end effector mobility. Examples of such improvements include increased instrument flexibility, better ergonomic positioning, hand tremor reduction, translation of motion frames of reference, telesurgery, robotic surgery systems and the like. ECS systems typically include more elaborate instruments and support structures when compared to traditional laparoscopic surgery and may also include the use of novel body entry devices and different points of entry compared to laparoscopic or other minimally invasive surgical techniques.

Electrosurgical systems have utilized Active Electrode Monitoring ("AEM") for several years, such as AEM monitor systems manufactured by Encision, Inc. of Boulder, Colo. These systems are generally described in U.S. Pat. No. 5,312,401 and related patents. Despite the success obtained, and increased patient safety realized, by the inventions embodied in the '401 patent, as well as the electrosurgical tools that embody those inventions, there remain certain problems and drawbacks when applied to ECS systems.

These drawbacks include, among other things, 1) the need to provide instrument shielding on structures that are not rigid shafts and that include complex articulating geometries found in ECS systems and tools, and 2) the need to monitor one or more non-electrosurgical instruments. As used herein, the term "cold instrument" refers to a surgical tool or device that does not have or is not meant to have electrosurgical energy actively applied to it or its end effector. These cold instruments can, under certain conditions, conduct electrical energy that can become harmful to the patient and cause burns. The same harmful conditions that can provide electrical energy to the cold instruments can also effect floating conductive surfaces that might also be in contact with the patient or operating room staff, such as the operating table or the mechanical support structure used to hold and control the ECS systems.

Current procedures used in minimally invasive electrosurgery utilize multiple access ports for the various instruments. Though devices such as the Encision AEM® monitoring system protect the active electrode instrument, the potential still exists that the surgeon might inadvertently or purposefully touch another instrument such as a grasper or optical scope with the active and electrically charged instrument. This additional instrument then has the potential to transfer electrical energy directly to the patient in an area that may not be visible to the surgeon. In addition, new surgical techniques involving single port access surgery (SPA), robotic surgery, and natural orifice transluminal endoscopy (NOTES) position the instruments in even closer proximity to each other and contain more non-referenced conductive surfaces that can inadvertently carry electrical energy. While SPA apparatus (instruments and cannulae) are generally not used for ECS systems as described above, they involve different points of entry compared to traditional laparoscopic surgery. For instance, SPA surgery might be used for cosmetic reasons, reduced pain, and reduced chance for herniation. Because all instruments pass through a single incision (e.g. the umbilicus) they are very close together and increase the likelihood of cross-coupling of energy compared to traditional laparoscopic surgery. This highlights the need for both active instrument protection and for cold instrument monitoring and protection.

Thus, there is a need for a better way to provide a monitored electrosurgical energy to the primary "hot" instrument while also monitoring for inadvertent stray electrosurgical energy in cold instruments and other conductive surfaces. In addition, because of the added degrees of freedom and the need to accommodate advanced monitoring techniques in the more complex and larger scale instruments being utilized in ECS surgical techniques, prior monitoring techniques used in rigid shaft embodiments are not adequate.

SUMMARY OF THE INVENTION

In accordance with one aspect, a surgical system comprises a device adapted to deliver a plurality of surgical instruments to a site within a patient's body, a first surgical instrument comprising an active electrode probe, a second surgical instrument for performing a non-electrosurgical procedure, a conductive shield surrounding the active electrode probe of the first surgical instrument and connected to a reference potential, and a cold instrument monitor connected to the second surgical instrument and to the reference potential.

In accordance with another aspect, a surgical system comprises a surgical control mechanism for delivering a plurality of surgical instruments to a site within a patient's body, the surgical control mechanism comprising a control arm for maneuvering at least one of the plurality of surgical instruments, a first surgical instrument comprising an active electrode probe having a tip and being adapted for connection to an electrosurgical generator for effecting at the tip thereof an electrosurgical procedure within a patient's body, a second surgical instrument for performing a non-electrosurgical procedure, a conductive shield surrounding the active electrode probe and connected to a reference potential, and a cold instrument monitor connected to the second surgical instrument and to the reference potential. In accordance with another aspect, any current which flows from the active electrode probe to the second surgical instrument is conducted to the reference potential.

In accordance with another aspect, an enhanced control surgery system for aiding in the performance of a surgical procedure comprises a surgical tool control arm having one or more interconnected and articulated members, a controller adapted to maneuver the surgical tool control arm, an active electrode probe having a tip and extending through the surgical tool control arm, the active electrode probe being adapted for connection to an electrosurgical generator, a conductive shield surrounding the active electrode probe, and an electrical terminal connected to the shield and adapted to connect the shield to a reference potential. In accordance with another aspect, the active electrode probe and the conductive shield are adapted to substantially conform to the movements of the surgical tool control arm.

Other aspects will become apparent to one of skill in the art upon a review of the following drawings and detailed description.

BRIEF DESCRIPTION OF THE DRAWINGS

Various aspects, objects and advantages, and a more complete understanding of the present invention are apparent and more readily appreciated by reference to the following Detailed Description and to the appended claims when taken in conjunction with the accompanying Drawings, wherein:

DETAILED DESCRIPTION

Figure 1A:
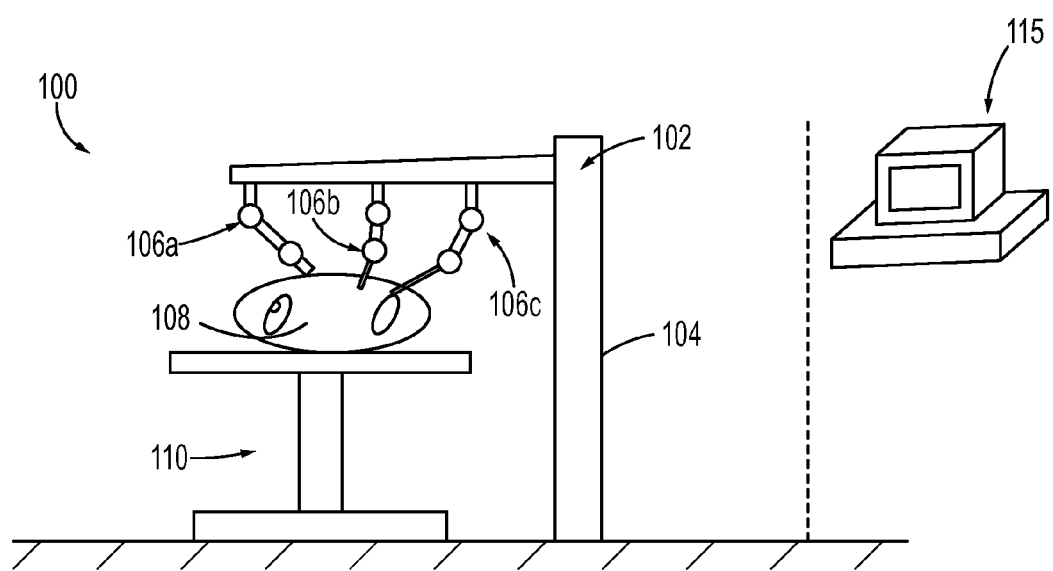
FIG. 1A is a generalized diagram of an enhanced control surgical system.

The term ECS refers to both Enhanced Control Surgery systems as a whole as well as one or more of the components utilized in such procedures. These may include robotic arms and the individual components, controllers, and other complex mechanical devices used in the robotic systems, as well as any specialty tools or structures used to perform the surgical procedure. While providing a heightened degree of control and accuracy, certain implementations of ECS may involve a field of view that is even more limited than in traditional laparoscopic surgery. This occurs in part because the surgeon may not have the ability to pan a camera inside the patient and may not have direct vision at the port sites. In addition, due to the small size of individual components (including conductors) in ECS and other flexible systems, there is an increased risk of electrical breakdown due to both mechanical and electrical stress. Breakdown may be within the instrument or in the conductor system and may include conduction to shielding components or to the ECS support structure.

ECS tools and systems offer the ability to deliver various forms of electrical power depending on the type of surgery or procedure involved. Thus, there is a need for shielding and protective monitoring in bipolar modes (both electrodes in instrument and both surgically active), sesquipolar modes (both electrodes in instrument but only one electrode surgically active) as well as monopolar modes (one electrode in instrument, the other as a remote return electrode) electrosurgical systems. In all electrosurgical modes the objective is to protect the patient and users from the harmful effects of insulation failure, capacitive coupling and current inadvertently conducted through cold instruments and support structures.

In ECS systems the potential for cross coupling between an active instrument and an adjacent cold instrument or other conductive object may need to be controlled differently than in open or laparoscopic surgery. This is at least partially due to the fact that there may be more conductive objects in closer proximity to each other combined with less opportunity for direct visualization. This is further problematic because an ECS tool may be activated either directly with controls near the patient, or remotely.

In ECS applications, surgery may also take place in an extremely confined space. This could be for example within an organ or the vascular system. In these situations an electrosurgical active electrode may contact other instruments not intended to be electrified, or contact other conductive objects within the body. Under these conditions it is desirable to limit energy delivery so that excessive heating to the conductive object or to body tissue does not occur. Under extreme conditions welding can occur between the electrode and the contacted object and this is particularly important to avoid.

Typically when there is sparking between metallic objects, there is a characteristic frequency spectrum of the conducted current that is different from the spectrum of current delivered to tissue in normal electro surgery. This spectral difference in active current of the electrosurgical system can be sensed and used to determine the presence of a fault condition.

FIG. 1A is high-level representation of a common embodiment of an ECS system 100. Major components of such a system include a support structure 102, actuation means 104, and one or more flexible or otherwise articulating elements or control arms 106a, 106b, and 106c. As with traditional surgical techniques, a patient 108 is supported on an operating table 110 positioned next to and/or underneath the surgical system 100. A control terminal 115, such as a computer or other interface, is available to interact with the ECS system 100 and is adapted to allow a user to control the one or more control arms 106a-106c in order to perform the surgical procedure. The control terminal 115 may be located adjacent to the ECS system 100 in the same operating room, may be in an adjacent (e.g., non-sterile) room, or may be at a remote site from the surgical procedure itself. Various computer screens and/or other monitoring devices may be located in and around the ECS system 100 in order to convey information to the operating room staff.

Figure 1B:
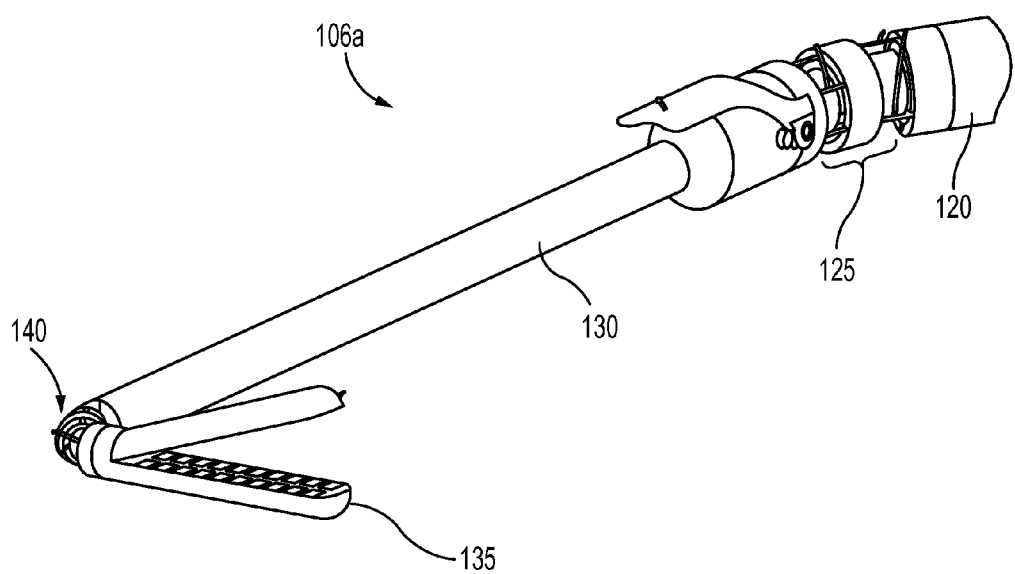
FIG. 1B is a drawing of one embodiment of a control arm used in an enhanced control surgical system.

FIG. 1B is representative of one of the control arm elements 106a from FIG. 1A and more particularly shows one embodiment of the articulating and movable nature of the control arm element 106a. Control arm 106a includes a connector 120 or other interface that mounts to or engages with the support structure 102. Control arm 106a ultimately interfaces with control terminal 115 where an operator or surgeon can control the movements of the control arm 106a. An articulation mechanism 125 connects to an elongated segment 130 and preferably provides three degrees of movement to the segment 130. The length of segment 130 varies in different embodiments depending on the specific type of procedure being effected. Articulation mechanism 125 provides a bendable and rotatable joint (also referred to as a wrist) for an operator to maneuver in order to move the segment 130 into a desired position in three dimensional space. A second articulation mechanism 140 connects the segment 130 with an end effector 135. In one embodiment, the end effector is an active electrode for performing an electrosurgical procedure. In FIG. 1B, the end effector is shown as a grasper. Various other end effectors may be utilized as well including both cold and hot instrument configurations.

Figure 1C:
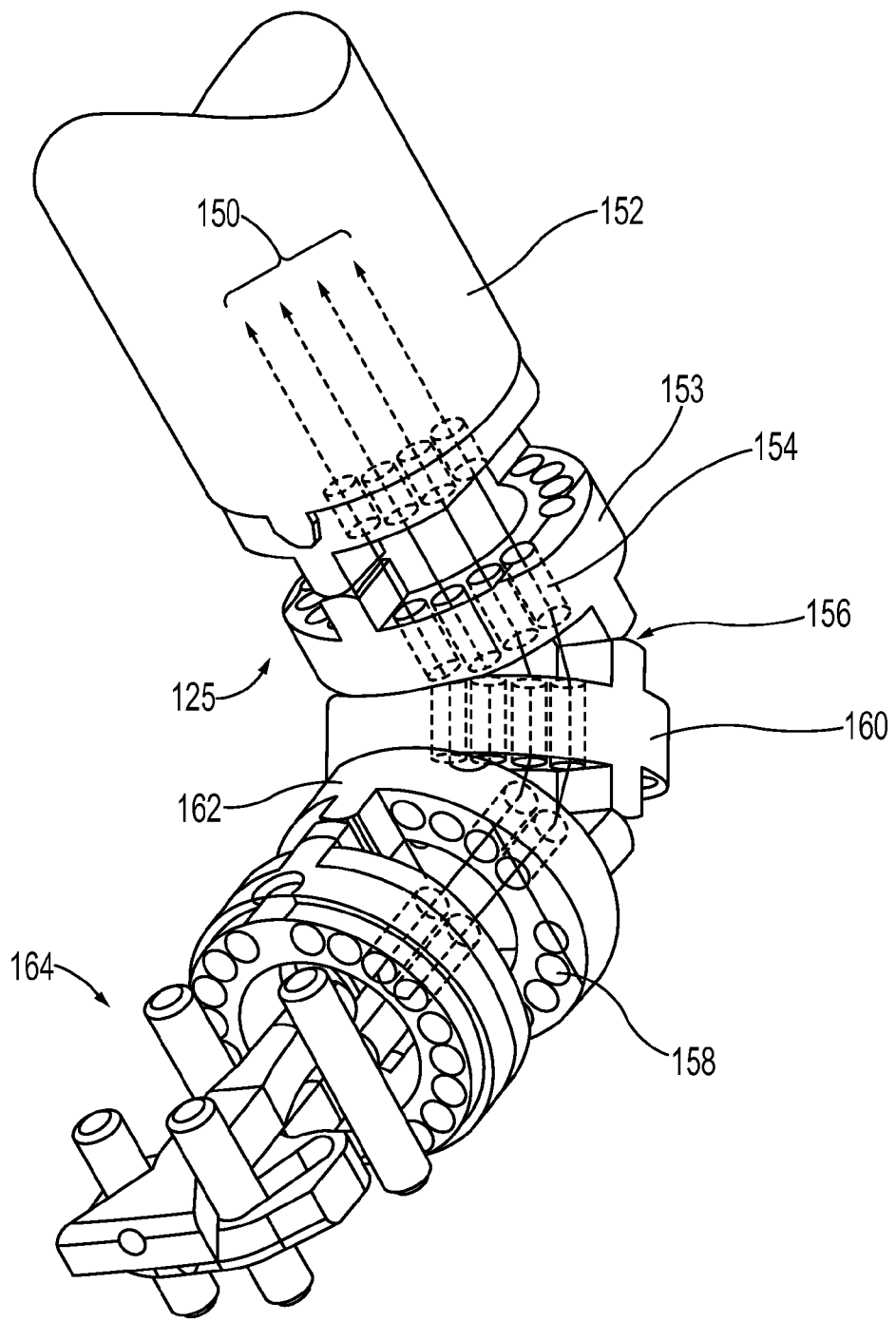
FIG. 1C is a detail of one embodiment of an articulated control arm member of an enhanced control surgical system.

FIG. 1C shows one embodiment of a detailed articulation mechanism 125. FIG. 1C is one type of "wrist" mechanism as can be seen by the ability of the joint to move in many degrees of freedom such as a human wrist can. Mechanism 125 includes interconnected sections 152, 153, 160, and 162 that rotate, pivot and bend with respect to each other. Section 152 is adapted to engage in one embodiment with an elongate member that in turn holds an end effector or other tool for performing a surgical procedure. Exemplary embodiments and further details of these types of complex ECS devices can be found in U.S. Pat. No. 6,817,974, the details of which are incorporated herein by reference. The aspects disclosed in the present application are meant to have applicability to these and related ECS control systems. Mechanism 125 further includes various passageways 154 and 158 that provide a path for one or more conductors or other control wires to pass from one end of the mechanism to the other, while also being capable of following the curves and other manipulations within the geometry of the mechanism 125. As shown in FIG. 1C, various control wires or other conductors 150 are able to pass to the distal end of the device that include an end effector.

As described in more detail below, an active electrode, as well as any shielding structure associated with that electrode, that extends through the entire element 106a (including mechanism 125 from FIG. 1C) needs to be able to function properly while flexing, bending and/or twisting through the articulation mechanisms 125 and 140.

Figure 1D:
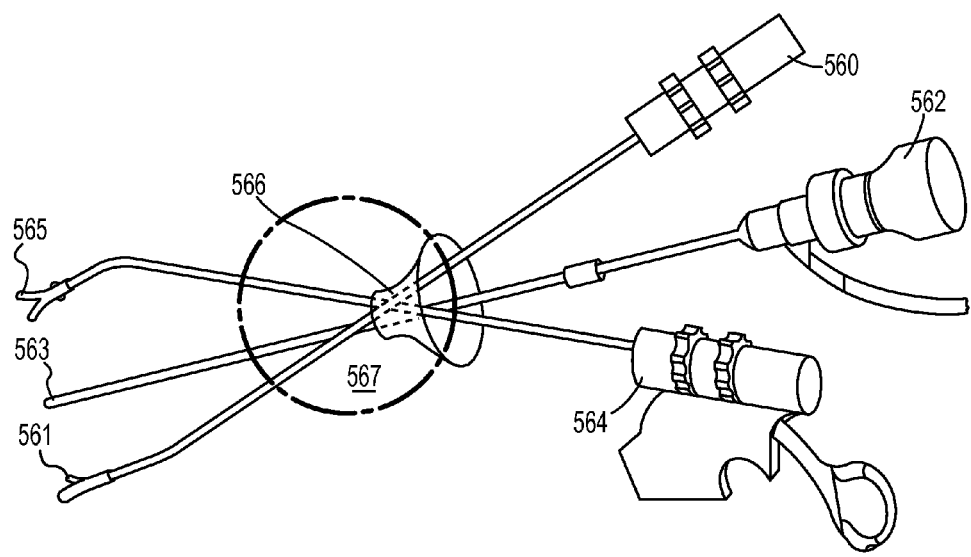
FIGS. 1D and 1E are depictions of a single port access procedure utilizing three surgical tools.
Figure 1E:
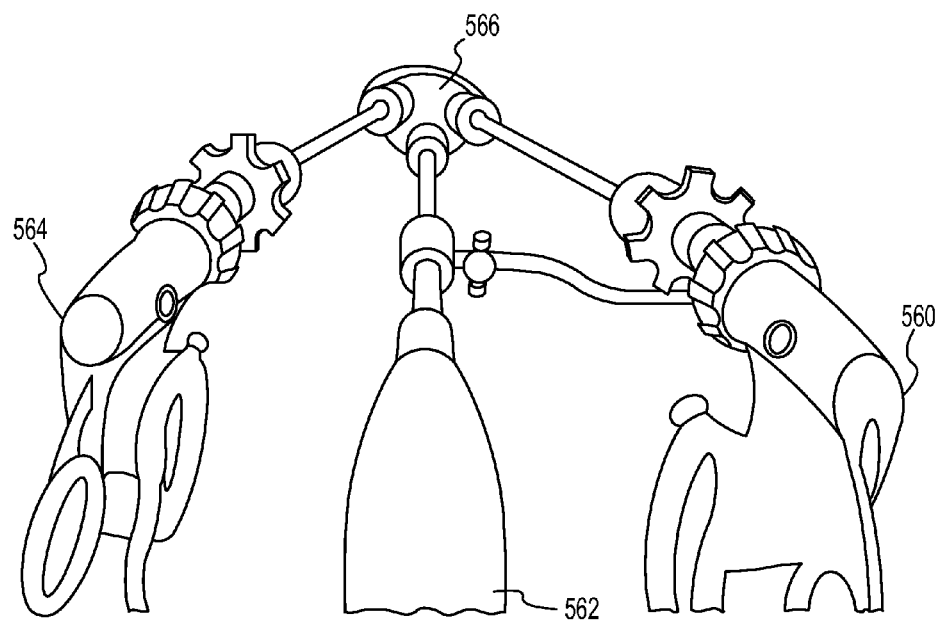

While particularly applicable to ECS procedures and the complex devices described above, the need to monitor the non-energized tools used in a surgical procedure also extends to single point access procedures. FIGS. 1D and 1E show the general orientation of three tools used in a single point entry procedure. An active electrosurgical ("hot") tool 560, a laparoscopic camera 562, and a third instrument 564 are all shown accessing a surgical site through a trocar cannula or other surgical tool introducer device at common entry point 566. In this embodiment, camera 562 and instrument 564 are "cold" and are thus not intended to carry electrical energy as the electrosurgical instrument 560 is meant to. The three surgical tools are meant to perform a surgical procedure at their distal ends 561, 563, and 565, and remain electrically isolated from each other. However, in this situation, the proximity of the three tools results in an area 567 where capacitive coupling from the electrosurgical instrument 560, a breakdown in the electrosurgical instrument's insulation, or inadvertent touching between the electrosurgical instrument 560 and one of the other instruments, will cause energy to be inadvertently transferred to the cold instruments 562 and 564 and eventually to the distal ends 563 and 565 of those instruments to a point in the body tissue where an electrical discharge is not desired. Among other things, monitoring and protection against these types of inadvertent burns is addressed by aspects of the present invention. Various new techniques can be used to detect these unsafe conditions.

Various Conventional electrosurgical applications (e.g. those involving a single rigid shaft tool) create a load impedance within a certain range. That load impedance range depends on the electrode size and tissue type, among other variables. If during an ECS procedure, an active electrode contacts a separate instrument or another conductive object that is not meant to be electrically active, the load impedance value may fall below the otherwise normal range. Thus, sensing the load impedance and using its value in a calculation can aid in the detection of a fault condition under these circumstances.

Also in conventional electrosurgical applications, the load impedance changes in a known fashion, generally starting at a relatively low value and progressing as the contacted tissue dries to a higher value. In an abnormal condition (e.g. where the active electrode contacts another conductive object), the pattern of impedance change may be downward with stabilization at a low value. One or more of this load impedance rate of change, the direction of change along the load impedance curve, and a spectral determination may then be used to detect any abnormal contact conditions. When such conditions are detected, a monitoring device is programmed to respond by reducing or ceasing the application of power to the active electrode.

Figure 2A:
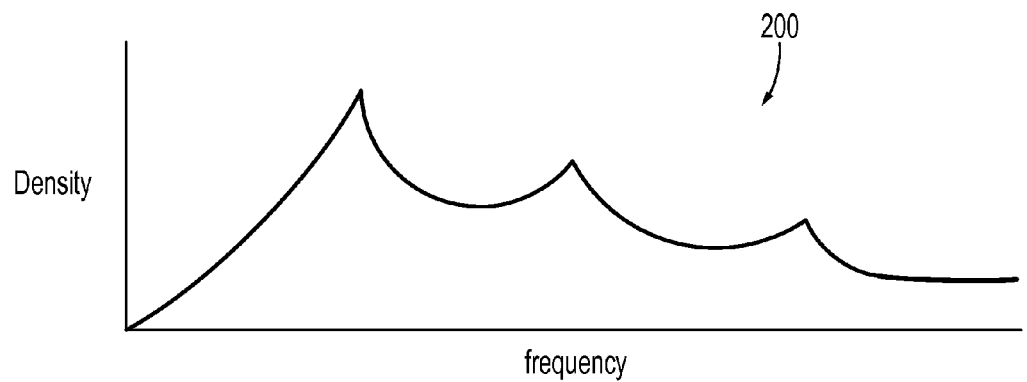
FIGS. 2A-2C are the various frequency spectrums exhibited during an electrosurgical procedure.
Figure 2B:
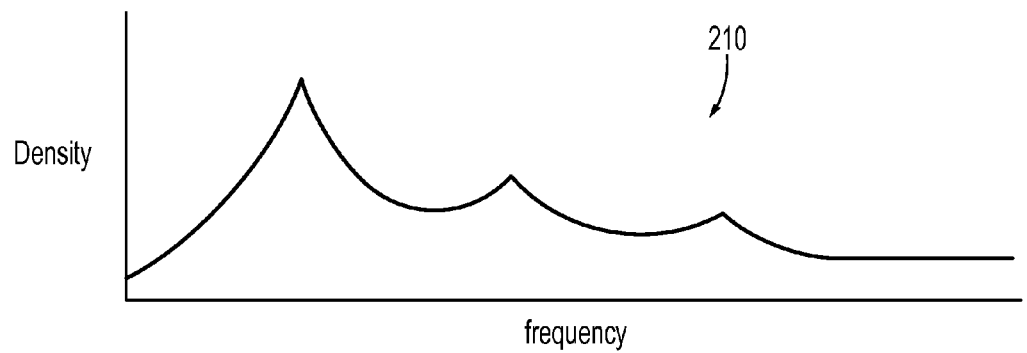
Figure 2C:
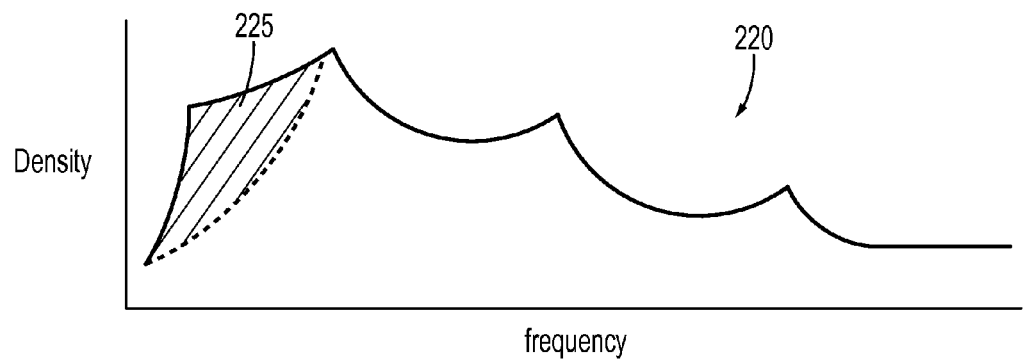

FIGS. 2A, 2B and 2C show various frequency spectrums under the different conditions described above and how contact with a normally non-energized instrument can result in the production of abnormal energy that needs to be avoided. For example, FIG. 2A shows a normal voltage waveform 200 under driving conditions, FIG. 2B shows the waveform 210 when the active electrode is in contact with tissue during a surgical procedure, and FIG. 2C shows the waveform 220 when the active electrode unintentionally comes into contact with a metallic or otherwise conductive object. The shaded area 225 in FIG. 2C represents the abnormal and unintended energy that ends up being delivered to the patient tissue under this condition. It is the abnormal condition represented by area 225 that needs to be monitored and/or prevented.

Figure 3A:
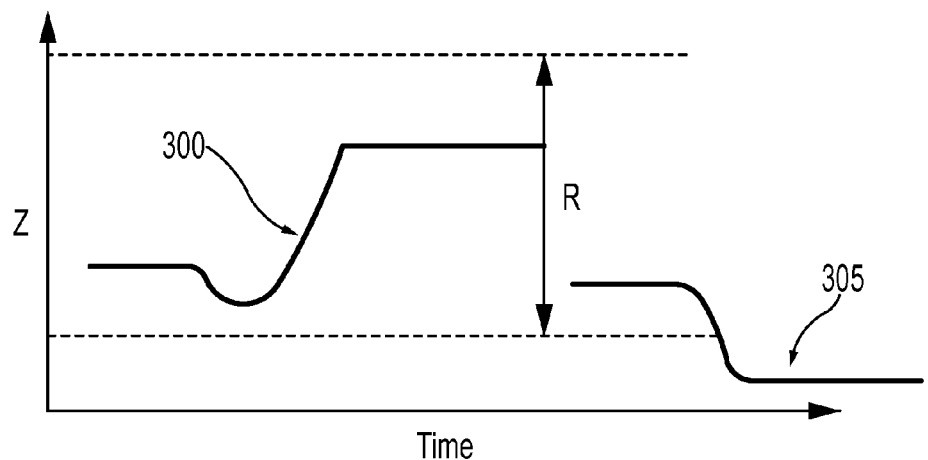
FIGS. 3A and 3B are diagrams that show the variations in impedance under conditions similar to those in FIGS. 2A-2C.
Figure 3B:
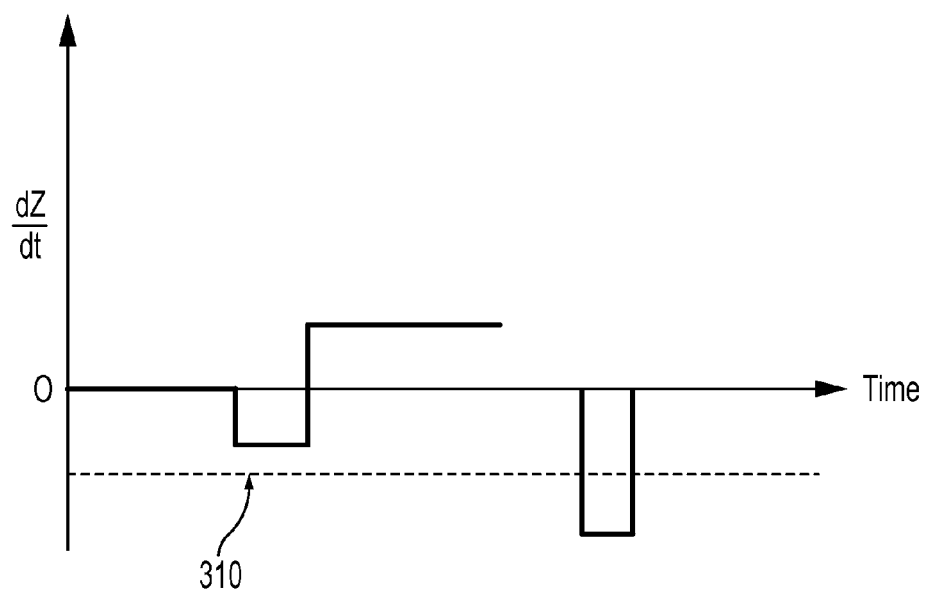

Turning to FIGS. 3A and 3B, these diagrams show the variations in impedance under conditions similar to those in FIGS. 2A-2C. FIG. 3A shows the expected variation of impedance under normal (300) and abnormal (305) conditions. The illustrated case shows the abnormal conditions placing the measured Z value below the normal range R. This example is indicative of a fault condition that would trigger the monitoring system to alter or cease power delivery to the active electrode.

FIG. 3B shows the expected variations in the time durations of impedance in the normal and abnormal conditions of FIG. 3A. Here, the abnormal condition 305 generates a negative spike which exceeds the expected range for normal conditions (the dashed "threshold" line 310) and is also indicative of a fault condition that would trigger the monitoring system to alter the user or cease power delivery to the active electrode.

Various embodiments are contemplated for sensing the presence of this abnormal energy. For example, an adaptive filter might be utilized that is sensitive to the driving waveform, and can be used to detect small differences in spectral energy. Either of the above evaluations can be used to determine the presence of a fault condition or they may be used in combination to determine a fault condition.

With the popularity of ECS systems providing additional degrees of freedom for an end effector, the application of shielded and safe (e.g. AEM) electrosurgery energy becomes more complex. The original format of a rigid shaft instrument that provides shielding and rigidity must be modified in many ECS applications.

Enhanced control systems including robotic systems, instruments having wrists, and instruments having flexible shafts impose increased stress on electrosurgical conductors both in monopolar and bipolar implementations. One example of this type of instrument is the device described in U.S. Patent Application 2006/0111210A1. This device is representative of the contrast with conventional laparoscopic instruments having rigid shafts and is representative of the problems solved by aspects of the present invention. These types of "bendable" and articulating shaft instruments pose an additional problem for the shielding used with traditional AEM technology due to the nature of the bending in the shield area. Conventional AEM instruments utilize a rigid tube conductor as the shield and it is this rigid tube that acts as a conductor for electrical shielding while also providing stiffness to the shaft. In accordance with various aspects of the present invention, the shield used in connection with an ECS system employing AEM monitoring does not have to be formed from a rigid material. This shield can be very flexible as long as it is capable of effectively carrying normal and fault current to the AEM monitor.

In accordance with one aspect, instrument shields may embody one or more flexible circuit concepts such as a metal coated flexible polymer as the shield conductor. Other embodiments of flexible shields may be conductive rubber, metal braids such as a coaxial cable, metal braids molded or extruded inside insulation material, or thin conductive film such as a metalized polymer. Further embodiments such as cloth with woven conductive fibers, metal or sprayed on conductors may be utilized as the shield. FIGS. 4A-4D show various embodiments of flexible circuits that may be utilized to construct the shield element in monitoring ECS systems. In addition, one or more of the concepts disclosed in U.S. patent application Ser. No. 11/740,483 may also be utilized to construct the shield conductors in an ECS system. The details of application Ser. No. 11/740,483 are incorporated by reference in their entirety into the present application. As used with the robotic graspers incorporated into many ECS systems, any of the previously described flexible shielding techniques and embodiments can be used to provide a flexible but electrically safe shield system for AEM technology. In accordance with another aspect, this technology can also be used for catheters or small probes used inter-luminally.

A thin film shield made from cloth, polymer, or other flexible materials as described above might not prevent an initial arc from generating a fault (e.g. broken insulation) condition by penetrating the shield. In other words, the flexible shield could have a hole burned through it when a fault occurs. However, the shield monitor would still sense the fault and begin the sequence of shutting down the energy. In tests the total reaction time is less than 10 msec. Therefore, the amount of energy dissipated would cause, at most, only superficial damage to the outer insulation of the shield. Accordingly, there is necessarily a trade-off between a thin flexible shield that might allow superficial damage and a substantially rigid and/or thick flexible shield that would prevent the energy from ever reaching beyond the shield in a fault condition but be more limited in its versatility in complex ECS systems. Further aspects and embodiments of AEM shields used in ECS applications are described below. It is contemplated that one or more of these embodiments made be used either alone or in combination depending on the specific application and the specific ECS system being developed.

Figure 4A:
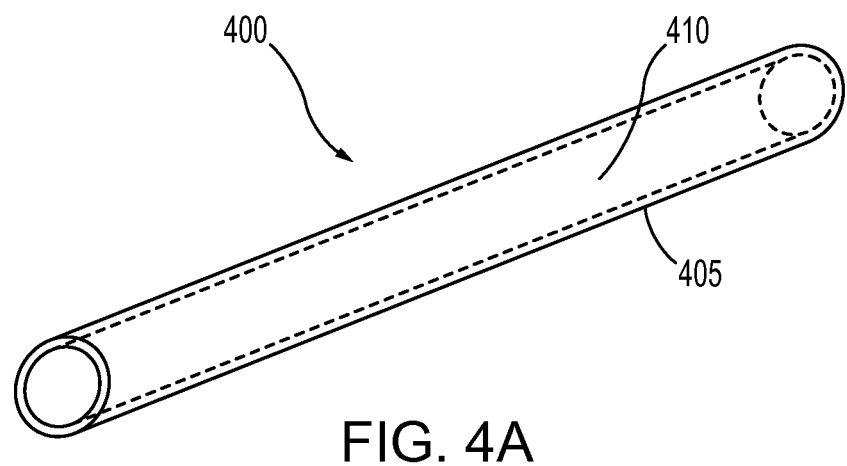
FIGS. 4A-4D show various embodiments of flexible circuits that may be utilized to construct the shield element in monitoring ECS systems.

In accordance with one aspect, FIG. 4A shows a shield 400 that comprises a metalized material 405 disposed over a polymer tubing 410. In another similar aspect, a conductive medium is disposed over a reinforced plastic or other nonconductive tubing. When utilized with a shield tube, these types of structures will prevent damage at a fault when the system initially breaks down and seeks electrosurgical return through the shield system. Systems such as these also have the benefit of mechanically preventing burns by absorbing fault energy until the AEM monitor can stop the power output.

Figure 4B:
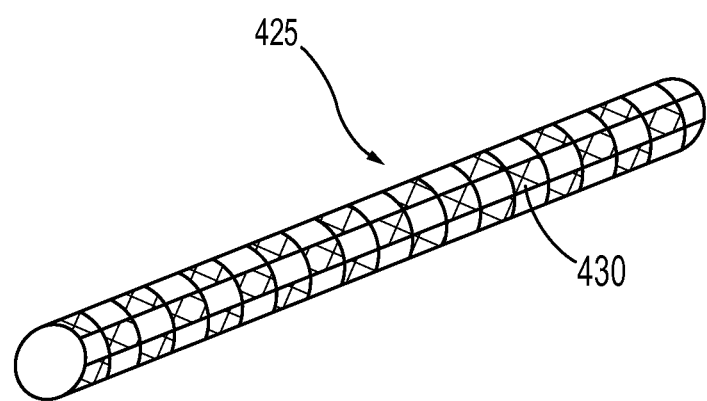

In accordance with another aspect, FIG. 4B shows a shield 425 that comprises a conductive cloth, wire mesh, or wire braid 430 utilized to form the conductive medium. Other examples include the use of a conductive polymer or elastomer, wire coils such as catheter coiling, embedded wires in a flexible structure or flex circuits such as those used in electronics and circuit board structures. While these particular flexible embodiments might not prevent a fault damage because of the potentially thin layer of material that is used, it can still utilize the AEM system to stop the power output from the generator. In one example test, it was observed that the worst case delay between insulation fault to power cut-off was about 7 msec, including circuit reaction time, and when a relay stopped current flow.

Figure 4C:
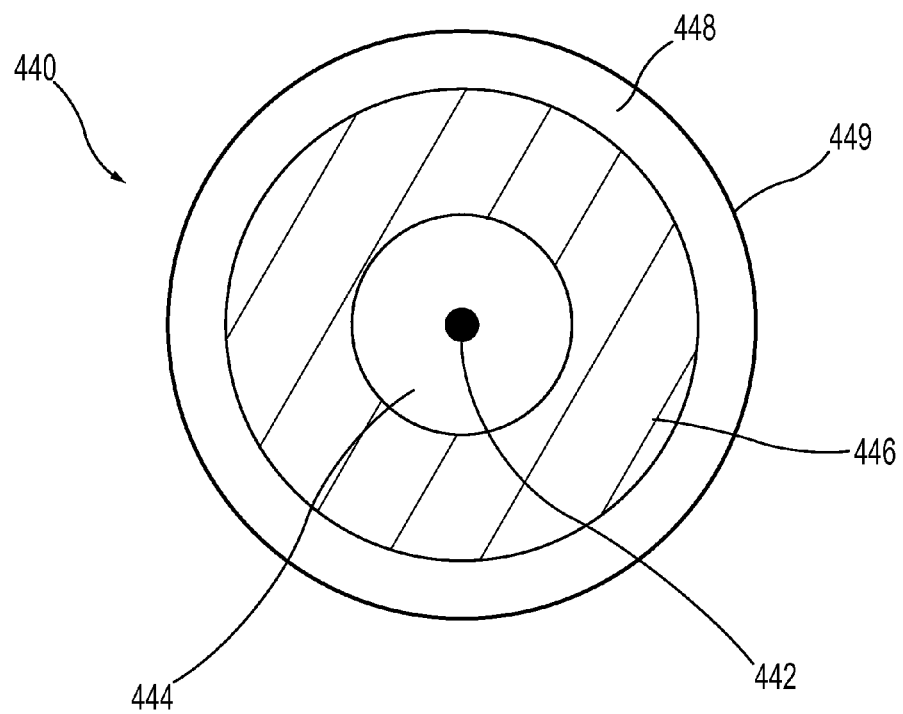

In accordance with another aspect, FIG. 4C shows the cross section of a coaxial cable 440 that includes a center conductor 442 surrounded by a solid layer 444, a foam layer 446 and a shield 448. An outer insulation layer 449 surrounds the cable 440. The cable 440 uses two types of primary insulation, one foamed material 446 with a very low dielectric constant and one of a conventional material 444. While the foamed material will withstand the voltage in most places, if the foamed material is used alone there will be insulation failures at modest voltages at particular points (because the randomly arranged bubbles in the foam line up between the conductors). The conventional material protects against failures at those points. Tests have shown good capacitance results with low heating, thus in most areas the foamed material is withstanding most of the voltage.

Figure 4D:
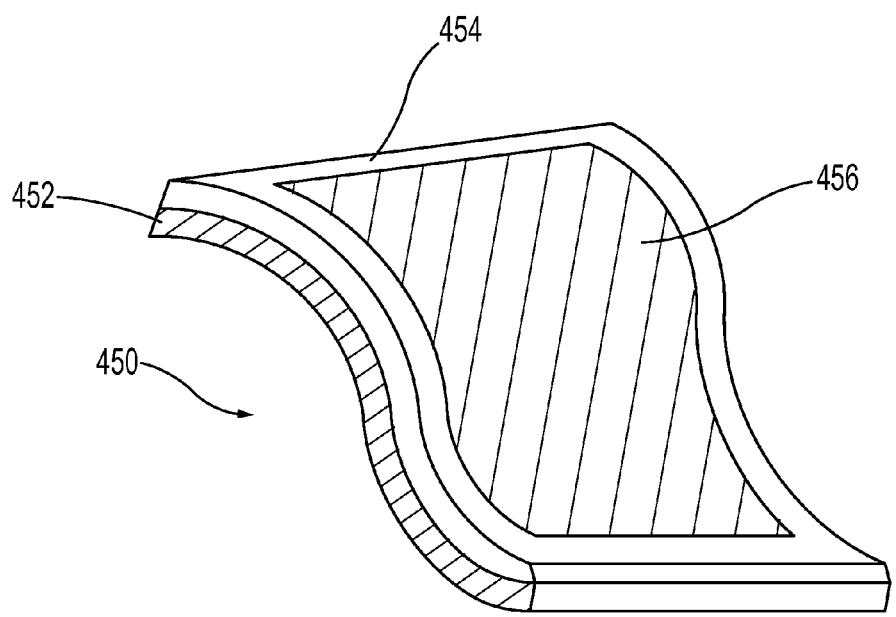

In accordance with another aspect, FIG. 4D shows an embodiment comprising a layered material based on a fabric matrix. Benefits of this embodiment include the ability to include such a material as any shape and the ability to cover the complex geometries found in ECS systems, such as wrists and other mechanical joints. A shield 450 includes insulating woven matrix 452 with a sprayed on conductor 454 and an insulating coating 456. Because of the flexibility of the shield 450, it can be formed into any shape, such as an insulting boot for a wrist element in an ECS system. In another embodiment the shield 450 is formed in place and mimics the outer surface of the instrument it surrounds.

The use of electrosurgical conductors in ECS systems has specific issues that need to be addressed in a monitored environment. As mentioned above, enhanced control systems may employ a wrist or other flexible element between the electrode and a support structure (See e.g. FIGS. 1B and 1C) and thus the active conductors and shielding conductors must also be flexible in order to follow the same physical path as the surgical devices and tools. In accordance with another aspect, to address this problem, the active and shield conductors may be run in a bundled cable assembly such as a coaxial cable where the shield conductors enclose the active(s) in a portion of the ECS assembly such as distal flexible elements. This arrangement permits the high-voltage conductors to couple capacitively or by breakdown to metallic components of the control assembly and or other end effectors which hold or manipulate tissue or organs during surgery. In these cases there tends to be increased capacitive loading, but also reduced opportunity for active electrical breakdown or capacitive coupling to mechanical components. Enhanced control systems will have many optical, mechanical, electronic, or hydraulic components contained in compact structures. Thus there is a need for all components, including the electrosurgical conductors to be compact. FIG. 1C described above shows an example of this compact embodiment in a wrist style tool and how all of the integrated components need to fit within a confined space that moves or otherwise articulates during operation.

A connector for the active electrode can be present at any point in the RF assembly. However any breakdown paths in the connector need to be controlled so that the most likely breakdown is from active to shield rather than to an outside conductor. Optimal locations for the connector are where the environment is dry.

In accordance with another embodiment, a flexible sheath or boot (reusable, limited-use or disposable) may be used to protect against electrical conduction from exposed components in the wrist area or other flexible portion of the ECS system and the patient or users. The sheath or boot may be entirely insulating or shielded with a conductor embedded in the insulation or on the surface of the insulation. The conductor may be connected to other conductive components of the ECS system or to a conductor dedicated for the purpose of conducting shielding currents to monitoring equipment. For example, the fabric matrix of FIG. 4C can be formed to fit over and contour with the surface of an ECS tool as shown in FIG. 1C. In another embodiment, a small caliber flexible AEM conductor may be run through one of the conductor channels 154 or 158 in the ECS wrist 125 of FIG. 1C.

In general, a shielded electrosurgical conductor may be made more compact than a non-shielded conductor. This is primarily because non-shielded conductors must be made with additional margins of safety against insulation breakdown, resulting in a larger diameter or overall footprint. In addition, the insulator in a non-shielded conductor must be large enough to minimize corona (the local breakdown of air near the outside of an insulated wire conducting high voltage electrosurgical energy). Corona is known to cause heating and produce ozone. Corona can also cause damage to other components of electrosurgical systems from associated chemical mechanisms.

In contrast, a shielded conductor can be constructed with a smaller margin of safety compared to a non-shielded conductor since any failure of the insulation is prevented from causing damage to patients, users, or equipment by the shield and a monitor that causes power shutdown before there is any significant damage. Also no corona is produced in a shielded conductor because there is no air subjected to high electrical field strength. These conditions result in a possible substantial reduction in conductor size. For example, typical non-shielded monopolar electrosurgical conductors measure 0.090 to 0.120 inches or larger in diameter. A shielded monopolar conductor can be made in the range of 0.040 to 0.070" in diameter. The resulting smaller footprint of shielded electrosurgical conductors give them greater utility when incorporated into monitored ECS system, particularly those embodiments using bundled cabling or other consolidated conductor arrangements.

As in traditional AEM systems, the shield in ECS and other flexible systems is connected to an electrosurgical return or other reference at patient potential. This is to provide a return path directly to the RF current source for capacitive and fault currents. It also provides the shielding with only a minor effect on RF leakage currents. Conversely, if the shield were returned to earth ground there would be a large increase in RF leakage current. This increase is undesirable from the standpoint of patient safety and also conformance with international standards.

Flexible micro-coax cable can be used in connection with the above described embodiments. In general, coaxial cable appropriate for electro-surgery monopolar outputs has high capacitance (20-50 pF/ft). However, the needs in an ECS system for small size, flexibility, and reduced coupling internally may be over a fairly short length, say 2-4 feet as opposed to the normal 10' monopolar conductors. A coaxial structure with a dual-layer internal insulation system can reduce the capacitance per unit length and thus increase the length possible for a given capacitance. In this embodiment, one layer is a conventional thermoplastic having a relative dielectric constant of 2.0 to 3.5. The second layer is a foamed fluorocarbon having a dielectric constant of 1.1-1.3. The net dielectric constant for a system appropriate for high voltage for example up to 6 KV electrosurgical energy transmission, is in the range of 1.2 to 1.5. This reduces the capacitance per unit length of the coaxial structure 30% or more compared to the use of a simple dielectric. Foamed material withstands the voltage in most places. However if the foamed material is used alone there will be insulation failures at modest voltages, for example 2 KV at particular points. This is because the randomly arranged bubbles in the foam line up so that there is insufficient insulation thickness in a particular line through the material. The conventional material protects against failures at those points. Tests have shown good capacitance results with low heating, thus in most areas the foamed material is withstanding most of the voltage.

In one example, a coaxial conductor was utilized with the following characteristics:

| Component | Radius (mil) | Description |
|---|---|---|
| Center | 6 | 25/44 |
| Pri insulation | 12.5 | FEP |
| Shield | 7 | Spiral 44ga 99% covered |
| Outer insulation | 4 | FEP |
| Total Diameter | .059" +/− .004 | |

As mentioned above, an ECS unit may employ a structure separately supported from the patient, surgeons, trocar cannulae, etc. These structures may be supported by a frame attached to the operating room (OR) table or OR floor (See e.g. FIG. 1A). Consequently, electrical breakdown and leakage may occur between the high voltage conductors and the ECS frame or other structure. Any such breakdown must result in a safe condition for the patient and users. The support may be comprised of conductive and insulating components. The ECS structure will likely have exposed and/or internal conductive components and insulating components.

In accordance with another aspect, an ECS system utilizes a specially designed electrosurgical monitoring system. In one embodiment, the monitor has specialized sensing algorithms for each of the different channels. Referencing potentials may include the return electrode, a reference potential electrode (RPE) earth ground, and a derived reference and may be different for the separate channels. One such system is described in co-pending U.S. patent application Ser. No. 12/257,562 filed on Oct. 24, 2008, the entire details of which are incorporated by reference into the present application. In another example, a dual channel monitoring system as described in U.S. Pat. No. 7,422,589 is utilized. The entire details of U.S. Pat. No. 7,422,589 are incorporated by reference into the present application.

In accordance with another aspect, internal ECS metallic components are monitored for high levels of current and/or power and referenced to the electrosurgical return. Exposed metallic components are monitored for low currents and/or powers and referenced to a return electrode (RE), reference potential electrode (RPE), or derived reference (DR). In some cases it may be desirable to utilize an earth ground or an operating room table reference. The electrode shield can be monitored for high levels of current and/or power and referenced to the electrosurgical return electrode (RE). Embodiments described within U.S. patent application Ser. Nos. 11/202,605 and 11/202,915 may be relevant in performing this type of function. The details of these applications are incorporated by reference in their entirety into the present application.

It is desirable to make the shielded flexible sheaths or boots described above thin for the purposes of minimizing size and for maintaining the flexibility of the ECS devices. However very thin shields may be limited in their ability to accept and conduct insulation fault currents. To compensate for this, these shields may be adapted to function with a fast-responding algorithm to provide for the possibility of temporary conduction lasting for example 1 msec to a delicate shielding coating that partially ablates during an insulation failure. It is anticipated that such a shield would have an RE reference, however RPE and DR references are also possible.

In accordance with another aspect, ECS monitoring systems may be constructed as follows in bipolar systems. Two patient-coupled conductors may be contained within a single shield conductor or they may each have a separate shield. The monitoring system is preferably calibrated to indicate that a fault condition may consist of either or both conductors breaking down to the shielding conductors or to metallic components of the ECS. Given that the shielding conductors are connected to either RE, RPE, or DR potentials, the breakdown would result in a significant fraction of the total current being returned through the referencing connection. Further, in a bipolar application the voltages from each of the active electrodes to the referencing electrode would be significant. No or low voltage from active to reference would be evidence of a possible insulation failure and that asymmetrical voltage condition would be a monitored parameter.

In accordance with another aspect, ECS monitoring systems may be constructed in sesquipolar systems. Sesquipolar systems are monitored similarly to the manner for bipolar systems except that a continuous low voltage between the surgically inactive electrode and the reference potential is considered a normal condition. Thus this condition would not generate a fault response from the monitoring subsystem.

In accordance with another aspect, the electrosurgical generators themselves may be optimized for ECS procedures. For example, the generator may have limited power and voltages, for example powers less than 80 Watts and open-circuit voltages in the range of 2-4 KV peak (compared to 300 W and 3-5 KV peak for standard monopolar generators). This allows the use of minimally thin insulations and small-gauge cables in and around highly compact mechanical assemblies such as wrists and elbows. This also results in lower shield currents in normal states of operation. In practice, the above limited amounts of power and voltage have been shown to be adequate for laparoscopic and most forms of endoscopic surgery not involving fluid environments.

In accordance with another aspect, the electrosurgical generator includes output circuitry to compensate for the loading of the capacitance present in the conductive shield and cabling. Testing has shown that in standard generators, performance degrades both in open circuit voltage and loaded power with increasing load capacitance. For example, 100 pF results in minimal degradation and 200 pF results in a significant but tolerable degree of degradation. In some implementations of ECS systems it may be desirable to support load capacitances in the 200-400 pF range. This can be presented by the combination of the electrode shielding components, the connectors, flexible shielded conductors and generator leads. Optimized generator output circuitry and internal feedback control that adjusts the output to account for load capacitance are examples of design features that permit calibrated operation in the presence of high load capacitance.

The electrosurgical generator can also be designed to operate with frequencies in the low region of the normal operating range of frequencies for general purpose generators of 200-800 KHz, for example in the range of 200-400 KHz. This will tend to facilitate the use of higher load capacitance by reducing the shield currents in the normal states of operation and allow more effective recognition of abnormal states of operation.

AEM monitoring components can be implemented in the generator itself in order to eliminate the need for a separate monitoring hardware. This would tend to reduce cost because of the elimination of the separate enclosure and power supply. It would also increase reliability because of the reduced cabling.

In accordance with another aspect, the potentials between the electrosurgical return electrode and earth ground may be measured and an upper limit placed on these potentials coupled with either an alarm, a reduction in applied voltage or the cessation of power in the event of a breach of the limit. The limits are important for patient safety, operator safety, and reduction of interference. Conditions that would generate high return-ground voltage consist primarily of an abnormally low impedance between active and ground. ECS systems may present low active to ground impedances due to the capacitance inherent in the physical construction of the system. Thus in these systems it may be desirable to include an electrical network between return and ground to maintain an adequately low return to ground voltage. The network may include capacitive, resistive and inductive components.

Normally patient to ground potentials are less than 100 Vrms. However in fault conditions such as the active electrode being connected to ground, the potential could rise to a value approaching 10 times that amount.

In accordance with another aspect, an electrosurgical system monitors for inadvertent electrosurgical energy in normally non-electrified ("cold") instruments and other large conductive surfaces. In known AEM implementations, the primary electrosurgical instrument is continually monitored for any stray electrosurgical energy via a multi-wire cord. The multi-wire cord provides both the active conductor for the electrosurgical and the reference wires for the shield which allows for continuous draining of any excessive energy due to capacitive coupling or insulation breakdown.

Current surgical procedures and especially new minimally invasive surgeries such as SPA procedures described above, place one or more instruments and cameras in close proximity to each other to minimize the entry points into the patient's body. Many of these tools and instruments are "cold" i.e. non-electrified and are generally used to view or handle the tissue in one way or another. Generally speaking, a "cold" instrument is any instrument that is not electrified via a direct and intentional electrosurgical connection. The various instruments used in SPA procedures usually consist of a camera, several graspers/dissectors, a "hot" instrument for performing the electrosurgical procedure, and various other manipulative instruments. It is desirable that the cold instruments also be protected and monitored to ensure that they remain cold. Most cold instruments are not properly insulated to deal with an electrical charge and become "hot" or otherwise electrically activated. Activated means that voltage is applied to the device. In the case of a cold instrument this can occur via touching the cold instrument with the tip of an activated hot instrument, through tissue that is contacted by an activated instrument and the device, via capacitive coupling from a hot instrument, and via insulation failure from a hot instrument. Even if these cold instruments are insulated, the surgical team is not controlling them as if they are hot and may not be utilizing the same precautions as are used when using an instrument that is intentionally hot. When the electrified instrument is being used, it can inadvertently transfer RF energy to another conductive instrument as described above. The cold instrument may also become energized through loose tissue in the surgical site, for example by a cold grasper holding separated tissue while the active electrode burns it resulting in a non-target tissue being burned by the cold instrument. A cold instrument may also become hot by the active cable being inadvertently attached to the wrong instrument.

Prior systems such as those taught by U.S. Pat. No. 5,312,401 teach that the most effective way to prevent stray RF electrosurgical energy from the hot instrument is to provide a monitored shielding system that actively drains any capacitive energy and monitors the draining (reference ground) circuit for excessive energy indicating a fault condition where the instrument's primary active conductor is shorting directly to the shield.

However, in order to protect the cold conductive surfaces from inadvertent or intended RF energy, each of the cold surfaces needs to be both monitored for excessive voltage and continually drained of any RF energy, for instance, by providing a referencing connection (Referencing Method). A second alternative also exists where the cold conductive surfaces are monitored for excessive voltage but any excessive energy is not drained (Monitoring Method). These two aspects are described below.

One method of achieving both referencing and monitoring is to provide reference potential for every conductive cold surface via wires that can conduct the energy back to monitoring circuits located in the AEM monitor. The conductive wires would work similarly to known shielding circuits contained within the monitor except each can be in a separate circuit where individual monitoring parameters can be adjusted to provide optimum referencing and monitoring. The reference conductors can be disposable, reposable (partially reusable) or reusable. In one embodiment, the wires will each electrically connect to the monitoring unit (AEM monitor) at the proximal end and to the conductive cold surface at the distal end. Connection at the conductive surface can be achieved in several ways depending on the surface. Details of various connection methods are described below. As the cold instrument or surface experiences inadvertent RF electrosurgical energy, the wire acting as a referencing surface will drain away any excessive energy. The monitoring system will also monitor for excessive voltage/current and control the electrosurgical source according to appropriate monitoring parameters.

In accordance with another aspect, each of the cold surfaces or instruments are monitored for excessive voltage. The monitoring of the cold surfaces triggers a monitoring base station (e.g. AEM unit) to shut down the electrosurgical source and provide an alert to the surgical team that a cold surface/instrument has experienced excessive RF energy and that appropriate action needs to be taken such as checking for patient burns around the instrument in question.

Figure 5A:
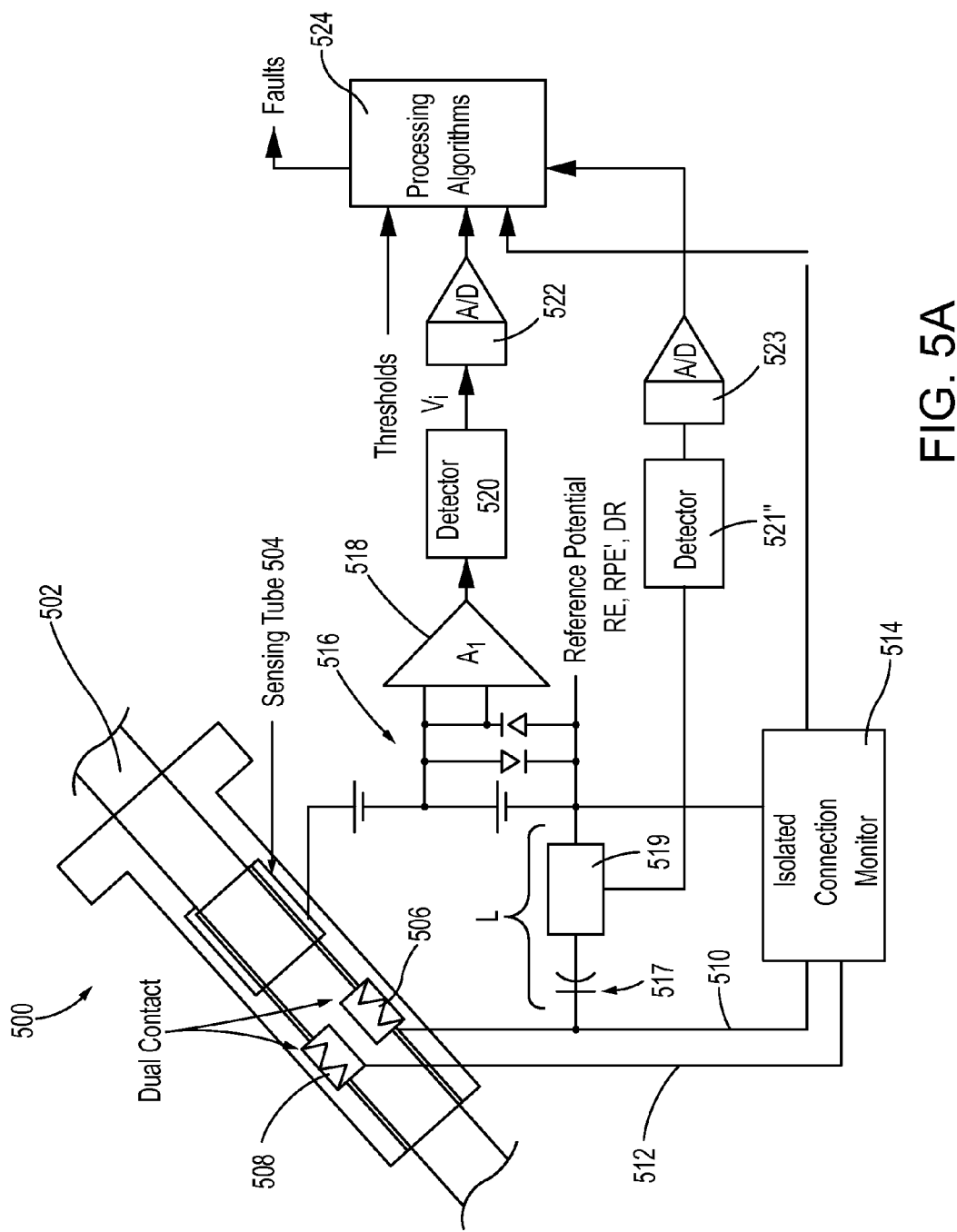
FIG. 5A shows one embodiment of a device for sensing the voltage on the surface of a cold surgical instrument.

With reference to FIG. 5A, an apparatus 500 for sensing voltage on the surface of a cold instrument is shown where a generalized instrument shaft 502 includes a plastic sensing tube or instrumented cannula 504 and a pair of dual monitoring contacts 506 and 508. Contacts 506 and 508 are connected by leads 510 and 512 to an isolated connection monitor 514. In accordance with one aspect, a method of providing electrical safety to cold instruments used during electrosurgery is as follows. The instrumented cannula 504 is used to provide both monitoring and referencing via dual contacts 506 and 508. Such a tool can be used for the following scenarios and instruments:

1) An uninsulated conductive instrument whose surface is exposed to the patient's tissues or users' hands. This type of instrument is never intended to be activated and become hot.

2) An instrument that is insulated except for a small area at the tip. If activated, this type of instrument is capable of protecting against conductive discharge through the insulation if the activation voltage is within the specification of the insulation.

3) A shielded instrument of the type described in U.S. Pat. No. 5,312,401 where the shield is connected to a reference potential through a monitor. The insulated exterior would not be capable of generating a significant patient or user burn even under the condition of an insulation fault because of the low voltage between the shield and the tissues.

In any of the above cases, contact sensors 506 and 508 are adapted to detect a voltage (V1) in the instrument 502. Two thresholds are set in firmware located and running within the connection monitor 514. These thresholds are compared with the detected voltage V1 and a determination is made about how to affect the applied voltage to the hot electrosurgical tool.

A first low threshold is set to result in a safe level of voltage for an uninsulated instrument. In conjunction or in the alternative a second threshold is set to a moderate level appropriate to a simply insulated cold instrument. A shielded instrument would not need to be voltage monitored, but the same threshold as for a simply insulated instrument could be applied.

The dual contacts 506 and 508 are sensed by the connection monitor 514 to determine if the instrument surface is conductive. A processing algorithm uses the conductivity determination to choose between a high-level or low-level threshold for an instrument voltage sensor. For example, the high level might be 2,000 V peak and the low level 50 V peak.

A voltage sensor 516 uses the sensing tube 504 in the cannula which measures the voltage of the instrument outer conductor. It has an outer insulator and may have an inner insulator. The sensing tube 504 may be directly connected to a conductive instrument, or capacitively coupled if there is an inner insulation layer. It will be capacitively coupled to an insulated instrument. The voltage sensor electronics has an input capacitive divider that interacts with the intentional and controlled capacitance of the sensing tube to give an acceptably accurate representation of the voltage on the instrument.

The output of a buffer amplifier 518 is detected at 520 (for example peak detected) for an input to an analog-to-digital converter 522 which than presents the data to a processor 524 implementing an algorithm that uses the data, thresholds, and time to make a determination of acceptable performance or a fault.

The dual contacts 506 and 508 may also be used to link a conductive instrument to a voltage reference. A link (L) may also include an isolation capacitor 517, a current sensor 519, a second detector 521, and second analog-to-digital converter 523 for a monitor. In this case the low voltage threshold described above is not used and instead a current threshold takes part in the fault determination. This implementation will generate fewer false-positive fault determinations than a low level voltage sensing due to capacitive coupling among SPA instruments.

The instrumented cannula system 500 is used to provide referencing and monitoring for example to a cold instrument having a conductive exterior such as an irrigation tube, and a cold instrument having an insulated exterior such as a cutting or grasping unit. As mentioned above, in the embodiment of FIG. 5A, two thresholds may be set in the firmware.

In one embodiment a cold instrument may be designed so that it can become energized. In this embodiment, cold instruments can be designed with an adequate outer insulation so that if the metallic tip (a housing or end effector) is touched with the active electrode, the patient would not be injured, assuming that the insulation was intact. In many cases, it is desirable to touch a cold instrument with the active electrode, for example, if the cold instrument is grasping a bleeding blood vessel. Given that the result of detection of a voltage is an alert to the user, it would be beneficial in some cases to inhibit this alert if the action is intended and safe. Possible design provisions include:

1. Providing a proximity detector in the instrument and cannula assembly so that the identity of the safe cold instrument is able to inhibit an alert.
2. Providing the function of No. 1 above through an optical property of the insulator recognized by a detector in the cannula assembly.
3. Providing a shield in the safe, cold instrument that would prevent coupling through the inner wall. The shield would be connected to the return.

In the diagram of FIG. 5A, the reference ground is provided to provide a stable (quiet from an RF standpoint) reference for the sensing amplifier $A_1$. Several options are available for the configuration of FIG. 5A.

In one embodiment, the reference ground should generally be an easily obtainable connection point, be electrically quiet (low RF noise or offset) and have some level of independence from the generator/monitor.

In another embodiment, the shield may be a direct connection to the shield in an AEM system. While this connection is easily obtainable in a hardware based system, there might be several tens of volts of RF noise due to the voltage drop of return current flowing through the return electrode connection impedance and also the shield current flowing through the shield coupling capacitor.

In one embodiment, the return electrode is a direct connection to the return electrode in an AEM system. The same noise problems exist as with the shield described above. The return electrode would then require reliable isolation because this is a patient connection.

In another embodiment, the reference potential electrode is as described in U.S. Pat. No. 7,465,302. This embodiment solves the problem of noise from return electrode voltage drop. However it would require a separate patient electrode which may or may not be housed in the same assembly as the return electrode. While this might introduce connection impedance, it should be of negligible consequence for this connection alone.

In another embodiment, the derived reference can be embodied as described in U.S. Pat. No. 7,465,302. This is a subsystem whose purpose is to avoid the need for a separate RPE and to provide an effective low impedance connection, while also providing an accurate representation of the voltage of the target tissue. It is estimated that this would present noise of only a few volts.

In another embodiment, the circuit ground is provided by the ground of the low voltage signal processing inside the AEM monitor. In any hardware based system this is easily obtainable. Its use would mean that no decoupling circuitry would be required for the detected signals. However, the noise could be expected to be significant.

In yet another embodiment, the environment reference is provided by coupling via an antenna to the general operating room ground. This is useful because it would not involve the design of the cannula or need a wired connection. However, the connection impedance would be extremely high and it could be expected to have noise equal to that of the circuit ground option. Additionally, there could be expected to be a large RF voltage component coupled from the instrument being measured which would reduce the effective differential signal level and also reduce accuracy.

In another embodiment, the abdominal wall reference is the potential of the abdominal wall in contact with the surgical cannula. A metal interior tube would be included in the cannula wall. This would be separate from the inner wall of FIG. 5A above and would be positioned to couple directly to the abdominal wall. It could conductively contact the tissue or capacitively couple to the tissue through a thin plastic insulation. This would provide a very quiet signal since there would be no significant electrosurgical current flowing through this region of the tissue.

Figure 5B:
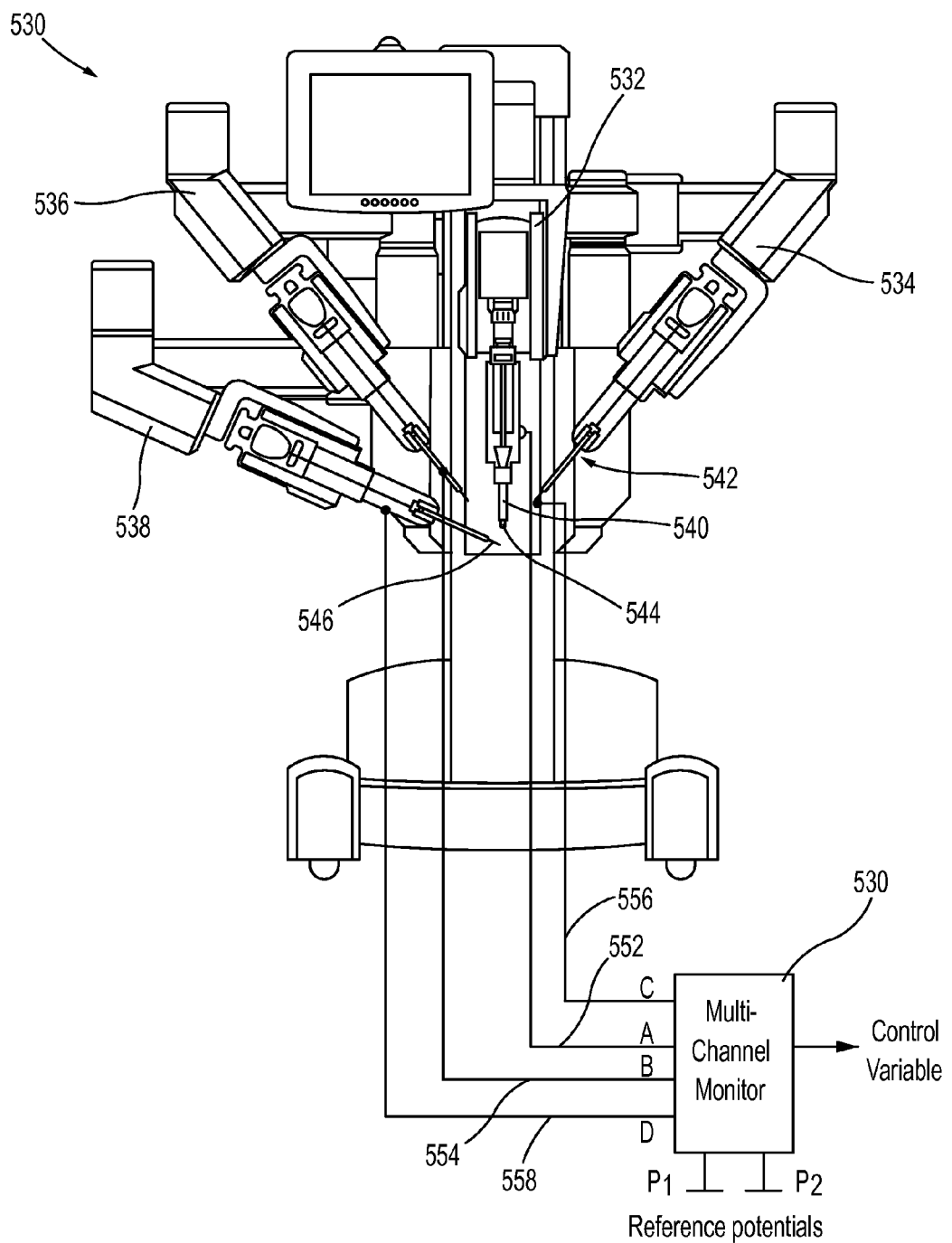
FIG. 5B shows one embodiment of a multi-channel monitoring system.

FIG. 5B shows a more specific embodiment of a multi-channel monitoring system used in a known ECS system. With reference to FIG. 5B, a complex robotic ECS system 530 typically includes two or more robotic arm assemblies 532, 534, 536, and 538, but more or less may be provided. Each robotic arm assembly is normally operatively connected to one of the master controls of a control station 115 or other surgeon console such as described in FIG. 1A. Thus, movement of the manipulator portion of the robotic arm assemblies is controlled by manipulation of the master controls at the control station 115.

Each of the robotic arm assemblies 532, 534, 536, and 538 comprises a linkage that supports and includes a removable surgical instrument or tool 540, 542, 544, and 546, respectively. The tools 540, 542, 544, and 546 of the robotic arm assemblies may include various types of end effectors and may also include an image capture device, an endoscope or a similar tool. Exemplary embodiments of such a surgical system can be found in U.S. Patent Application No. 2009/0192524, the details of which are incorporated herein by reference in their entirety.

Another embodiment of achieving referencing in a system such as that described in FIG. 5B is to provide conductive channels for every potentially dangerous conductive cold surface in order to conduct the energy away from the surface. In accordance with this aspect, a multi-channel monitor 550 is connected to a plurality of monitoring channels 552, 554, 556, and 558. Each of the channels 552, 554, 556 and 558 consists of a conductor (e.g. a wire), a monitoring channel, and a reference potential. A potentially dangerous conductive cold surface is any surface that can come in contact with a patient or user that is not intended to conduct energy such as the tools 540, 542, 544, and 546 of the robotic arm assemblies described above. The reference conductors can be disposable, reposable (partially reusable) or reusable. In one embodiment, the wires will each electrically connect to the monitor at the proximal end and to the conductive cold surface of the tools 540, 542, 544, and 546 of the robotic arm assemblies at the distal end. Connection at the conductive surface can be achieved in several ways depending on the surface. As the cold instrument or surface experiences inadvertent RF electrosurgical energy, the wire connecting the referencing surface will drain away any excessive energy. As shown in FIG. 5B, the types of surfaces that may be referenced include the body of a driving mechanism, a non-insulated instrument shaft, an instrument tip, and/or a support structure. Any of these surfaces may come in contact with a patient or a user and cause injury if significant energy is transmitted at the point of contact. Different reference potentials may be assigned for each conductive surface being monitored.

It is desirable to implement monitoring in each referencing channel so that dangerous conditions will cause an alert and excessive energy will be prevented. The monitoring system 550 monitors for excessive voltage, current, power or energy as, for example, disclosed in U.S. patent application Ser. No. 12/257,562 and controls the electrosurgical source according to appropriate monitoring parameters which may be different for each type of surface. The monitoring of the cold surfaces triggers the monitoring system to reduce power or shut down the electrosurgical source. An alert is provided to the surgical team that a cold surface/instrument has experienced excessive RF energy and that appropriate action needs to be taken such as resolving an instrument collision and checking for patient burns around the surface in question.

In accordance with another embodiment, the monitoring circuit comprises a base unit (such as a modified AEM monitor) and individual sensor tags. Each of the tags attaches directly to the conductive surface to be monitored. The tags can be wired, or wireless and provide communication back to a central location where the base unit is connected to the electrosurgical power source and capable of shutting down ESU power should excessive voltage be detected at a tag. In various embodiments the tags include RF tags such as found on most merchandise or clothing, most of which tend to be passive. In addition, active tags can also be utilized (active meaning they have their own power source) usually found in tracking/inventory applications. The tags can be disposable, reposable (have both a disposable and reusable element), or reusable. The tags can also have visible/audible indicators. The indicators can provide one state such as a green light for working, and a second state for alert mode such as a flashing red light indicating the tag has sensed excessive RF energy. The indicators will help the operating room staff quickly identify which of the multiple tags has de-activated the ESU and therefore needs to be accessed for damage to the patient.

For both the referencing and the monitoring methods described above, the wired or wireless tags can attach to the multiple "cold" surfaces in various ways. For the cases where the metal of the surface to monitor is directly exposed, the wired or wireless tag needs to be simply attached, electrically conductive, to the metal surface. This can be achieved through adhesive, mechanical attachment or other methods that place a conductive surface of the wire and/or tag directly to the metal cold surface. In this case, the monitoring assembly can be fully disposable, or have a disposable element such as the adhesive tag and a reusable element such as the wire. For the case where the cold surface to be monitored cannot be directly accessed by the tag or wire, a capacitive assembly is integrated with the surface to be monitored. For example, many of the current electrosurgical instruments are insulated to prevent accidental exposure of active components if the instrument is used "hot." Therefore, direct access to the metal of the instrument is not possible without damaging the instrument. By placing a conductive tube around this instrument and electrically monitoring any current flow through this tube, or voltage if a known reference is used, RF energy can be detected. The "tube" thus forms a capacitor with the instrument. The tube can take many shapes and forms so long as a capacitor with sufficient surface area is formed. Examples are described below.

Figure 6:
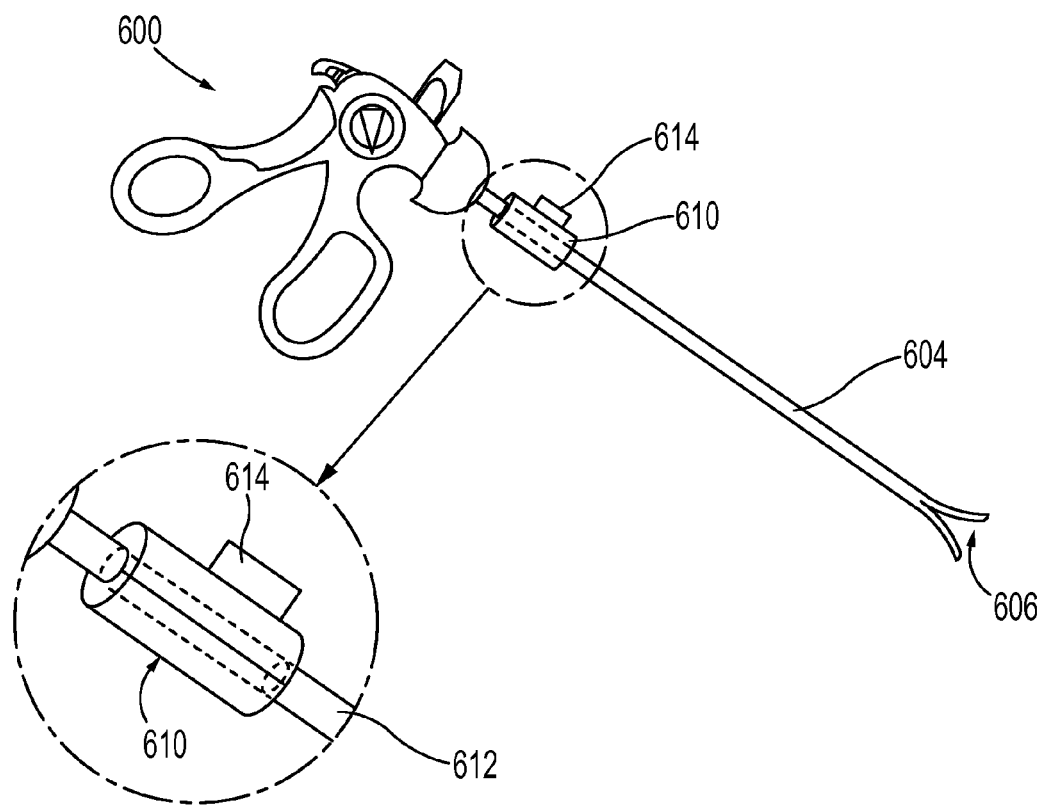
FIG. 6 shows one aspect of a device constructed in accordance with aspects of the present invention.

FIG. 6 shows one embodiment of a surgical instrument 600 that generally includes a handle portion 602, a shaft 604 and an end effector 606. In order to monitor the voltage present in the instrument shaft 604, a clamp sensor 610 including an RF tag 614 is placed at some point along the length of the shaft 604. The clamp sensor 610 forms a capacitive tube that can monitor voltage in the instrument shaft 604. The voltage is in one embodiment referenced against the surrounding air for any high occurrences of voltage that might indicate a dangerous situation for the patient. If high voltage is detected, the sensor 610 communicates with the AEM monitor which then inactivates the electrosurgical generator. As described above, the tag can be wireless or wired directly to the AEM monitor and can also include an LED indicator to show which of the wireless tags sensed the over-voltage.

Figure 7A:
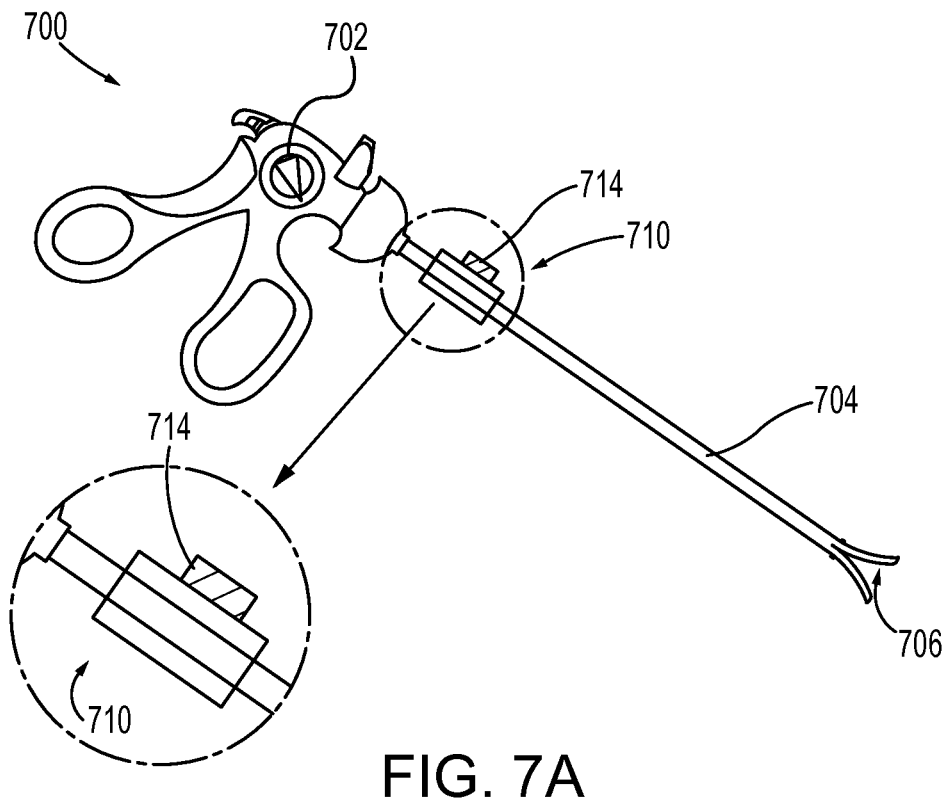
FIGS. 7A and 7B shows another aspect of a device constructed in accordance with aspects of the present invention.
Figure 7B:
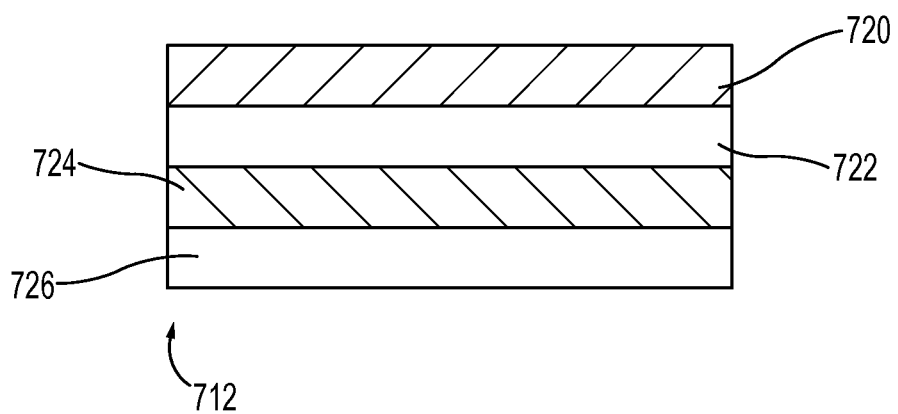

FIGS. 7A and 7B show another embodiment of a sensor used to monitor any cold instruments or other surfaces. In FIG. 7A a surgical instrument 700 generally includes a handle portion 702, a shaft 704 and an end effector 706. In order to monitor the voltage present in the instrument shaft 704, an adhesive sensor 710 that includes sensor layers 712 and an RF tag 714 is placed at some point along the length of the shaft 704. The sensor 710 forms a capacitive structure that can monitor voltage in the instrument shaft 704. If high voltage is detected, the sensor 710 communicates with the AEM monitor through the tag 714 which then inactivates the electrosurgical generator. FIG. 7B shows a detail of the sensor 712 including an insulation layer 720, a conductive layer 722, a second insulation layer 724 and an adhesive layer 726. While the sensor 710 is shown attached to a surgical instrument, the nature of this embodiment lends itself well to attaching to other flat surfaces such as an operating room table, the robotic arm of an ECS surgical system or even a person performing some aspect of the surgery.

Figure 8:
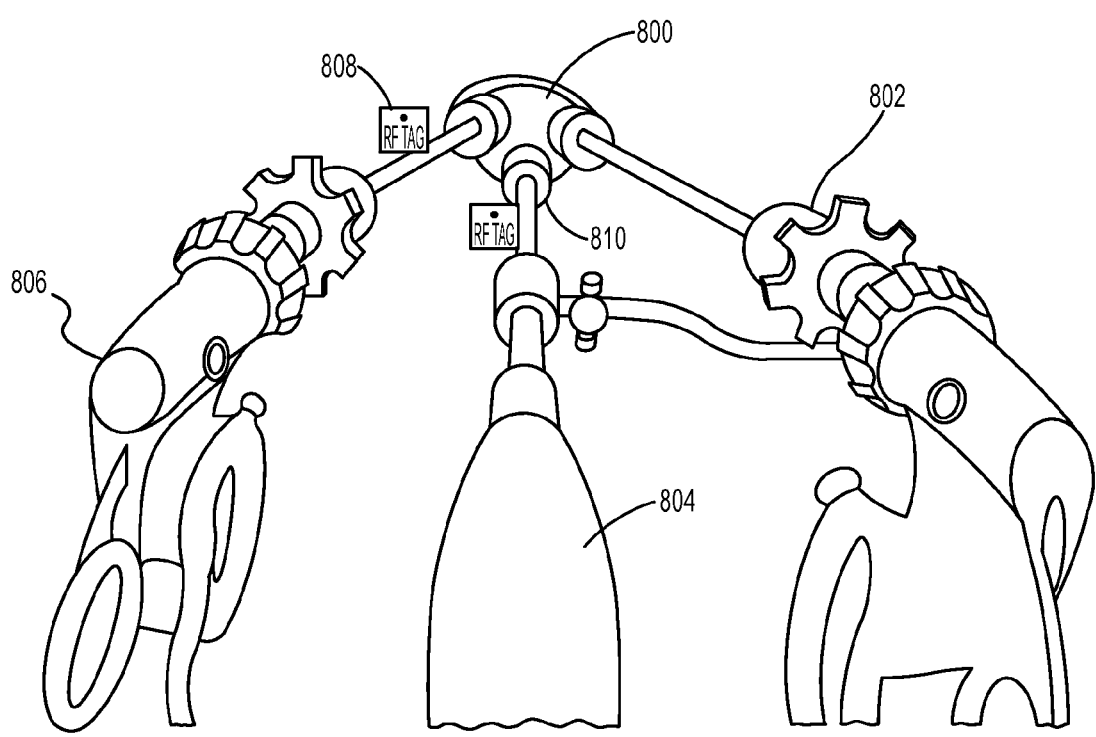
FIG. 8 shows a view of a single point entry procedure in accordance with various aspects of the present invention.

FIG. 8 shows a view of a single point entry procedure performed through a single incision 800 that utilizes one hot electrosurgical instrument 802 and two cold instruments 804 and 806. In one embodiment one of the cold instruments is a camera, although the same principles apply to any cold instrument used in such a procedure. In FIG. 8, cold instrument sensors 808 and 810 are attached to cold instruments 806 and 804 and monitor those instruments for any undesired voltage and relay this information back to the monitor for action that may need to be taken such as shutting down power to the electrosurgical instrument 802. In the embodiment of FIG. 8, the sensors can utilize either of the clamp or adhesive style sensors described above.

In another embodiment, the sensors can be rechargeable and available for use from a docking or other storage and/or charging station. At the discretion of the operating room staff, one or more sensors can be applied to any surface that may need monitoring for voltage or electrosurgical energy. Depending on the procedure, more or less of the sensors may be necessary or otherwise called for. Either of the clamp or adhesive style of the sensors described above are easily applied to instruments and/or other surfaces at a moments notice and at the discretion of the operating room staff.

Figure 9:
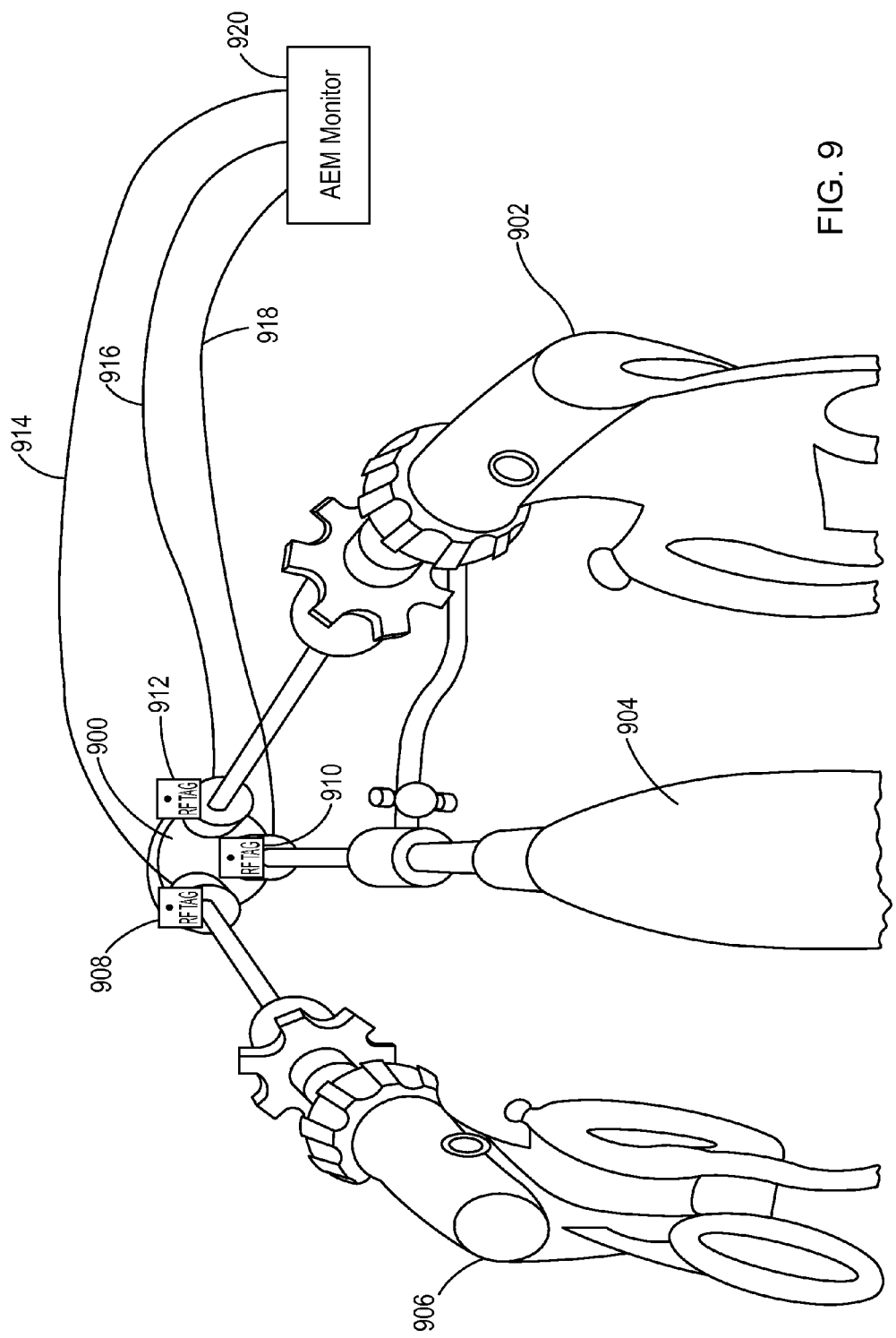
FIG. 9 shows a view of a single point entry procedure in accordance with another aspect of the present invention.

FIG. 9 shows a wired version of the sensors where three instruments 902, 904 and 906 are each accessing a surgical site through a single incision 900. Sensors 908, 910 and 912 are coupled to the three instruments, and are wired back to an AEM monitor 920 through conductors 914, 916 and 918. In this embodiment, the sensors are incorporated into the cannulas of the instruments 902, 904 and 906 and are generally not removable or interchangeable by a user. Instead, an OR staff person would connect each of the sensors to the AEM monitor 920 with the conductors 914, 916 and 918. This wired embodiment provides for a continuous drainage of current for any of the instruments.

Figure 10:
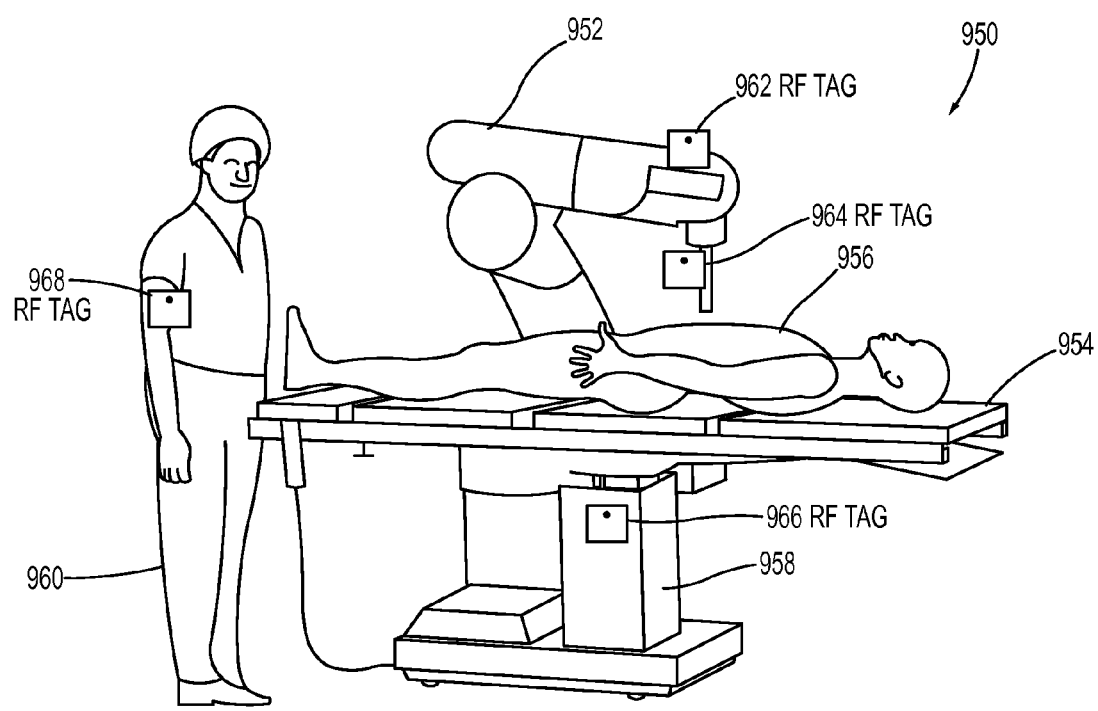
FIG. 10 shows a generalized ECS system setup that utilizes cold tool monitoring in accordance with various aspects of the present invention.

FIG. 10 shows a generalized ECS system setup 950 that utilizes cold tool monitoring as described above. The system 950 includes an ECS system 952 coupled or otherwise in communication with an operating room table 954 upon which a patient 956 is positioned. The OR table 954 may include other structures and/or surfaces such as a table mount 958. OR staff or surgeon 960 is present at some point during a surgical procedure. Sensors 962, 964, 966, and 968 are placed at various points in the system. In the example of FIG. 10, a sensor is placed on the ECS system, any tools or other actuation devices coming from the ECS system, the operating table, the table mount and the OR staff person. As can be appreciated, any surface that is desired to be monitored can have a sensor included and that is tied back to a monitoring device such as an AEM monitor.

The above connection methods provide several alternatives that can minimize cost, ease of attachment, variations of surfaces to monitor, and preference of the surgical team although alternative connection methods may also be used such as clip-on brackets, elastic or rigid straps, magnetic strips, or fasteners.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A method of monitoring and referencing a cold surgical instrument during an electrosurgical procedure utilizing more than one surgical instrument, wherein at least one of the surgical instruments is an electrosurgical instrument adapted to deliver electrosurgical energy, the method comprising:
providing a sensor proximate to the cold surgical instrument;
detecting an impedance of a circuit that includes the cold surgical instrument and the electrosurgical instrument during the electrosurgical procedure;
detecting a voltage in the cold surgical instrument through the sensor;
setting a first voltage threshold in a connection monitoring device;
comparing the detected voltage with the first threshold voltage;
determining whether the voltage represents an unsafe patient condition;
determining whether the impedance, a load impedance rate of change, a direction of change along a load impedance curve, or a spectral determination represents an abnormal and unintended contact condition between the cold instrument and the electrosurgical instrument;
altering the delivery of power to the electrosurgical instrument based on a determining of the unsafe patient condition or a determining of the abnormal and unintended contact condition.

2. The method of claim 1 further comprising coupling the cold surgical instrument to a reference voltage.

3. The method of claim 1, further comprising providing an audible alert if the detected voltage is greater than the first voltage threshold.

4. The method of claim 1, further comprising setting a second voltage threshold in the connection monitoring device and comparing the detected voltage with the second threshold voltage.

5. The method of claim 1, further comprising providing a detector proximate to the cold surgical instrument, wherein the detector identifies the cold surgical instrument.

6. The method of claim 1, further comprising altering the delivery of power within 10 msec of a fault.

7. The method of claim 1, further comprising altering the delivery of power within 10 msec of detecting the abnormal and unintended contact condition between the cold surgical instrument and the electrosurgical instrument.

8. The method of claim 1, further comprising providing two reference potentials.

9. The method of claim 2, further comprising the determining of the abnormal and unintended contact condition.

10. The method of claim 9, further comprising comparing a waveform of the energy delivered to a patient with a normal waveform under a set of driving conditions.

11. The method of claim 10, further comprising determining that the waveform of energy delivered to the patient comprises a voltage density that is greater than a normal voltage density under the set of driving conditions.

12. The method of claim 11, wherein the set of driving conditions comprises a frequency.

13. The method of claim 1, comprising:
altering the delivery of power to the electrosurgical instrument based on the determining of the abnormal and unintended contact condition.

14. A method of monitoring and referencing a cold surgical instrument during an electrosurgical procedure utilizing more than one surgical instrument, wherein at least one of the surgical instruments is an electrosurgical instrument adapted to deliver electrosurgical energy, the method comprising: detecting a voltage in the cold surgical instrument during the electrosurgical procedure in order to detect an unsafe patient condition; detecting an impedance over time of a circuit that includes the cold surgical instrument and the electrosurgical instrument during the electrosurgical procedure in order to detect an abnormal and unintended contact condition between the cold instrument and the electrosurgical instrument; determining that at least one of a load impedance rate of change, a direction of change along a load impedance curve, or a spectral determination represents the abnormal and unintended contact condition between the cold instrument and the electrosurgical instrument; and altering the delivery of power to the electrosurgical instrument based on the determining that the abnormal and unintended contact condition is represented.

15. The method of claim 14, comprising determining that the load impedance rate of change represents the abnormal and unintended contact condition between the cold instrument and the electrosurgical instrument.

16. The method of claim 14, comprising determining that the direction of change along the load impedance curve represents the abnormal and unintended contact condition between the cold instrument and the electrosurgical instrument.

17. The method of claim 14, comprising determining that the spectral determination represents the abnormal and unintended contact condition between the cold instrument and the electrosurgical instrument.

18. A method of monitoring and referencing a cold surgical instrument during an electrosurgical procedure utilizing more than one surgical instrument, wherein at least one of the surgical instruments is an electrosurgical instrument adapted to deliver electrosurgical energy, the method comprising: detecting a voltage in the cold surgical instrument during the electrosurgical procedure in order to detect an unsafe patient condition; detecting an energy delivered to a patient during the electrosurgical procedure; comparing the energy delivered to a threshold energy; determining whether the energy delivered to the patient is an abnormal and unintended energy caused by a contact condition between the cold instrument and the electrosurgical instrument, based on an impedance of a circuit including the cold instrument; and altering the delivery of power to the electrosurgical instrument based on the determining of the abnormal and unintended energy delivered to the patient.

19. The method of claim 18, further comprising:
detecting the impedance over time during the electrosurgical procedure.

20. The method of claim 18, further comprising:
determining that at least one of a load impedance rate of change, a direction of change along a load impedance curve, or a spectral determination represents the abnormal and unintended energy.

21. The method of claim 18, further comprising:
determining that the contact condition is unintended.

* * * * *